(12) United States Patent
Rice et al.

(10) Patent No.: US 7,894,996 B2
(45) Date of Patent: Feb. 22, 2011

(54) STRUCTURE OF THE HEPATITIS C NS5A PROTEIN

(75) Inventors: Charles Rice, New York, NY (US); Timothy Tellinghuisen, Royal Palm Beach, FL (US); Joseph Marcotrigiano, New Brunswick, NJ (US)

(73) Assignee: The Rockefeller University, New York, NY (US)

( * ) Notice: Subject to any disclaimer, the term of this patent is extended or adjusted under 35 U.S.C. 154(b) by 460 days.

(21) Appl. No.: 11/817,309

(22) PCT Filed: Feb. 28, 2006

(86) PCT No.: PCT/US2006/006847

§ 371 (c)(1),
(2), (4) Date: Sep. 11, 2008

(87) PCT Pub. No.: WO2006/093867

PCT Pub. Date: Sep. 8, 2006

(65) Prior Publication Data

US 2009/0004111 A1    Jan. 1, 2009

Related U.S. Application Data

(60) Provisional application No. 60/656,375, filed on Feb. 28, 2005.

(51) Int. Cl.
  *G01N 23/00* (2006.01)
  *G06G 7/58* (2006.01)
(52) U.S. Cl. .......................................... 702/19; 703/11
(58) Field of Classification Search ........................ None
  See application file for complete search history.

(56) References Cited

U.S. PATENT DOCUMENTS 6,524,589 B1 *   2/2003   Reichert et al. .......... 424/228.1
2002/0142387 A1  10/2002  Seki et al.

OTHER PUBLICATIONS

Tellinghuisen et al., "The NS5A Protein of Hepatitis C Virus is a Zinc Metalloprotein", the Journal of Biological Chemistry, Nov. 19, 2004, p. 48576-48587, vol. 279 No. 47.
Love et al., "Crystal Structure of a Novel Dimeric Form of NS5A Domain I Protein from Hepatitis C Virus", Journal of Virology, May 2009, pp. 4395-4403, vol. 83, No. 9, American Society for Microbiology.
Marcotrigiano et al., "Purification and Crystallization of NS5A Domain I of Hepatitis C Virus", Hepatitis C: Methods and Protocols, Second Edition, 2009, vol. 510, pp. 85-94, Humana Press.

(Continued)

*Primary Examiner*—Suzanne M. Noakes
(74) *Attorney, Agent, or Firm*—Thompson Coburn LLP; Charles P. Romano

(57) ABSTRACT

The present invention provides a crystallized N-terminal domain of an NS5A protein of hepatitis C virus, methods of producing the same and methods of use thereof. The present invention also relates to structural elements of the N-terminal domain of hepatitis C virus NS5A protein, and methods of inhibiting hepatitis C virus infection, replication and/or pathogenesis, by interacting with the same.

8 Claims, 8 Drawing Sheets

OTHER PUBLICATIONS

Penin et al., "Structure and Function of the Membrane Anchor Domain of Hepatitis C Virus Nonstructural Protein 5A", The Journal of Biological Chemistry, Sep. 24, 2004, pp. 40835-40843, vol. 279 No. 39.

Tellinghuisen et al., "Structure of the Zinc-Binding Domain of an Essential Replicase Component of Hepatitis C Virus Reveals a Novel Fold", Nature, May 19, 2005, pp. 374-379, vol. 435.

* cited by examiner

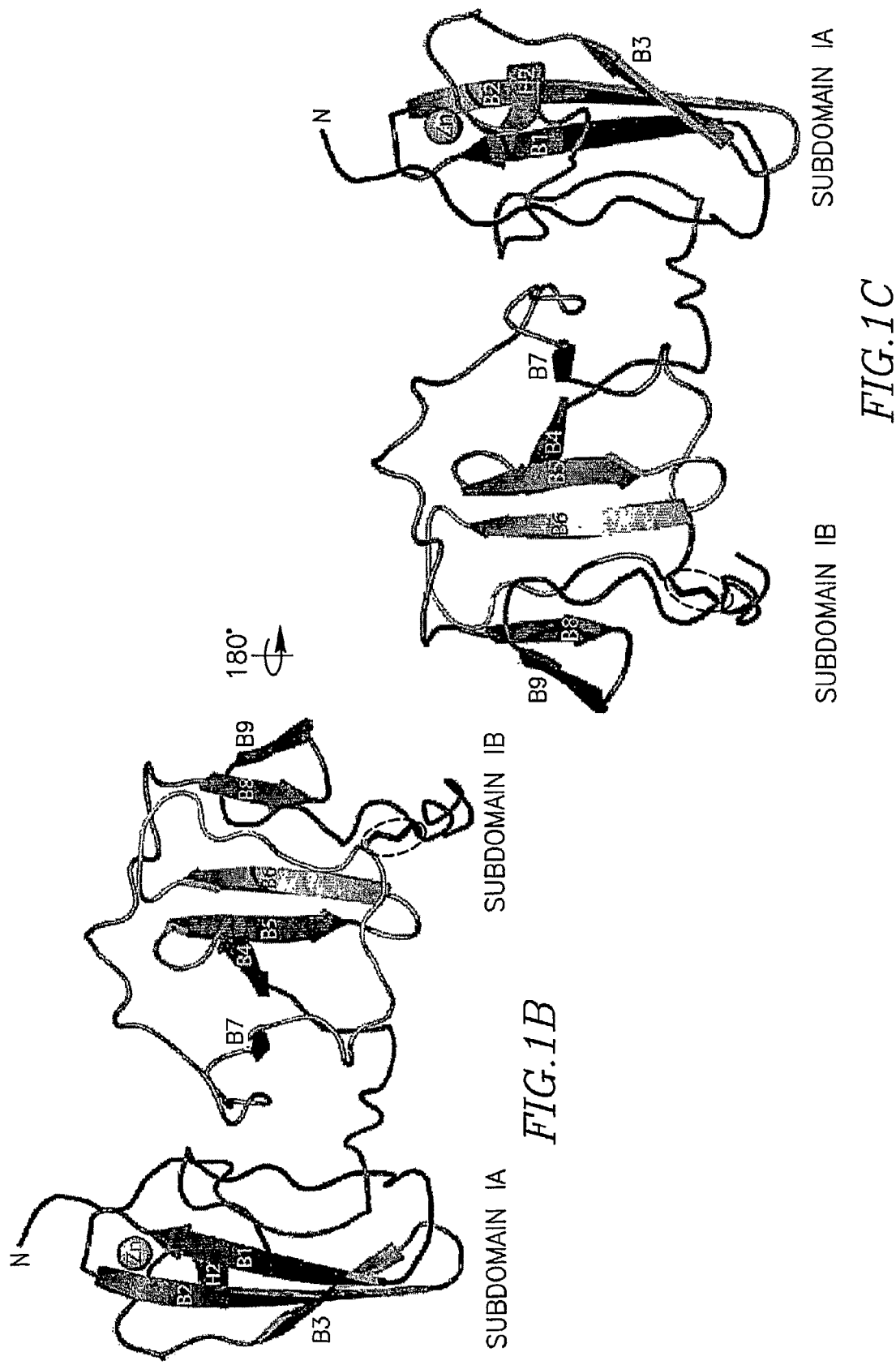

SUBDOMAIN IA                SUBDOMAIN IB

SUBDOMAIN IA                SUBDOMAIN IB

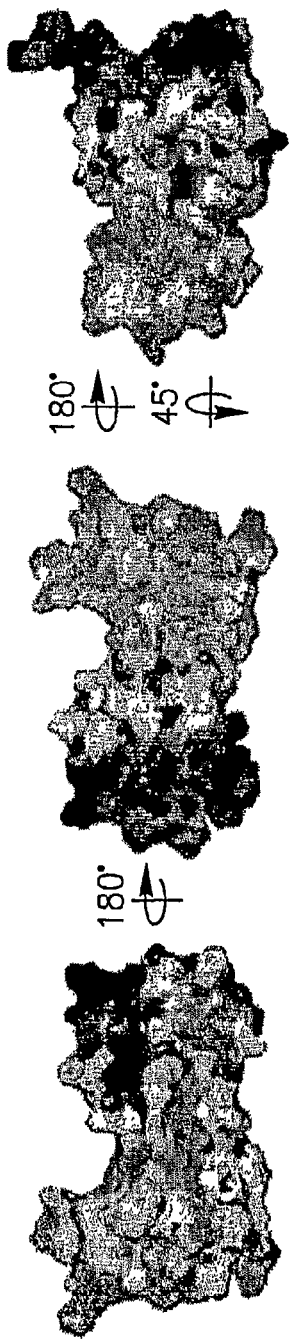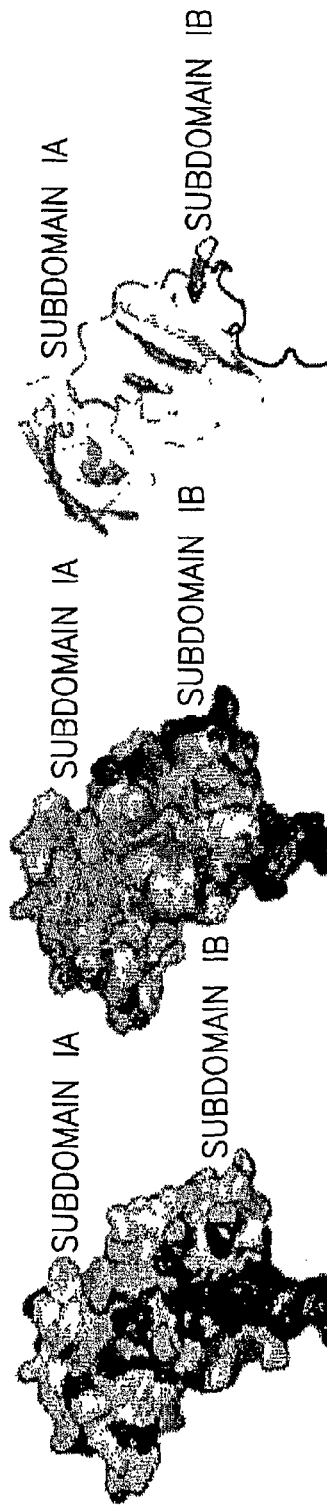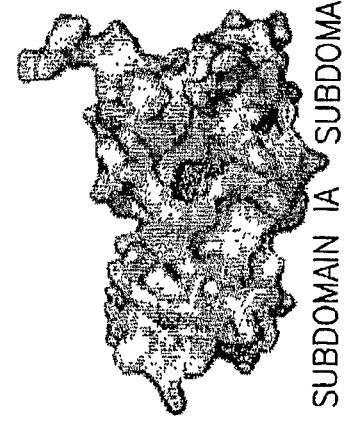
FIG. 3A
FIG. 3B
FIG. 3C
FIG. 3D
FIG. 3E
FIG. 3F

STRUCTURE OF THE HEPATITIS C NS5A PROTEIN

CROSS-REFERENCE TO RELATED APPLICATIONS

The present application claims the benefit of PCT/US2006/006847, filed Feb. 28, 2006 and entitled "Structure of the Hepatitis C Virus NS5A Protein", which claims the benefit of U.S. Provisional Application Ser. No. 60/656,375, filed Feb. 28, 2005, and entitled "Structure of the Hepatitis C Virus NS5A Protein". Both PCT/US2006/006847 and U.S. Provisional Application Ser. No. 60/656,375 are incorporated herein by reference in their entirety.

FIELD OF THE INVENTION

This invention provides crystallized N-terminal domain of an NS5A protein of hepatitis C virus, methods of producing the same and methods of use thereof. The present invention also relates to structural elements of the N-terminal domain of hepatitis C virus NS5A protein, and methods of inhibiting hepatitis C virus infection and/or pathogenesis, by interacting with, or interfering with the same.

BACKGROUND OF THE INVENTION

Hepatitis C virus (HCV) is a member of the Flaviviridae family of enveloped, positive-strand RNA viruses and constitutes the sole member of the genus *Hepacivirus*. HCV is a significant pathogen, with nearly 3% of the world's population, roughly 170 million people, persistently infected. Despite significant efforts, no vaccine exists for HCV, and current anti-viral therapeutics are inadequate for the majority of patients. The sequence diversity of HCV is complex, with virus organized into 6 distinct genotypes and over 30 subtypes. Additionally, HCV exists as many closely related viral sequences, termed quasi-species, in the infected individual, making specific pharmaceutical targeting of HCV proteins problematic due to the rapid evolution of escape mutants. It is increasingly evident that a broad collection of specific, pan-genotypic antiviral drugs targeting multiple essential viral functions, in addition to the current non-specific viral therapies, will be required for effective global control of HCV.

Considerable progress has been made in characterization of HCV in the decade and a half since it's discovery as the causative agent of non-A non-B hepatitis. Much of this knowledge is based on autonomously replicating HCV RNA replicons, as no cell culture system or small animal models exist for the propagation of HCV. The genome of HCV consists of a ~9.6 kb RNA molecule containing a single open reading frame flanked by highly structured 5' and 3' non-translated regions (NTR). Viral RNA is translated to generate a polyprotein precursor via an internal ribosome entry site within the 5' NTR. The polyprotein undergoes a complex series of cleavage events to yield the ten mature HCV proteins. Once processed, the HCV proteins assemble into the membrane associated RNA replicase that, in combination with undefined cellular factors, constitutes the machinery required for HCV RNA synthesis. Characterization of the replicase has defined the protease/helicase NS3 protein, the NS4A cofactor, the NS4B integral membrane protein, the NS5A protein, and the NS5B RNA dependent RNA polymerase as essential components. Crystal structures have been determined for at least some of these proteins, including NS3/NS4A and NS5B. These structures represent only two thirds of the proteins required for RNA replication, leaving an incomplete picture of the replicase. Nonetheless, these structures have allowed the development of exciting new HCV specific pharmaceuticals. To better understand the replicase and fuel further drug development, obtaining structural information for the remaining components of this machinery is of paramount importance. This is perhaps most evident for the enigmatic NS5A protein.

NS5A is a large (56-58 kDa) hydrophilic phosphoprotein of unknown function. The protein is post-translationally associated with ER derived membranes via an N-terminal amphipathic α-helix buried in the outer leaflet of the membrane. Recent work has proposed a three-domain model for NS5A organization and demonstrated the N-terminal domain (domain I) coordinates a single zinc atom per protein molecule. Mutations disrupting the membrane anchor or the zinc-binding site are lethal for RNA replication, suggesting a direct role for NS5A in this process. Additionally, the ability of adaptive mutations in NS5A to greatly stimulate HCV replication suggests an important role for this protein as a regulator of RNA replication. NS5A phosphorylation varies with replication efficiency, suggesting an interaction of NS5A with a cellular kinase(s) regulates RNA replication. NS5A appears to directly interact with all of the viral components of the replicase, and the interaction with the viral polymerase modulates the activity of this enzyme in vitro. These data collectively suggest NS5A serves as both an active replicase component and a regulator of replication. The modulation of replication by NS5A has been proposed to represent a switch between the replicative form of the viral RNA and a form of RNA amenable to virion biogenesis. This switch may involve the release of NS5A from the replicase or the conformational alteration of NS5A such that it is then free to interact with a variety of cellular components. NS5A interacts with proteins involved in membrane morphology and vesicular transport, suggesting it alters membranes for replication or virion assembly. NS5A interacts with many proteins in mitogenic and apoptotic signalling, resulting in the modulation of cellular growth and survival that may be important for the development and maintenance of HCV persistent infection. The alteration of these pathways by NS5A may represent a causative link between HCV infection and hepatocellular carcinoma (HCC). NS5A may be involved in another aspect of long-term viral persistence, the escape from the cellular antiviral response via the inhibition of the activity of the double stranded RNA dependent protein kinase (PKR). The interactions of NS5A with the host cell are far more complex than alluded to herein and the relevance of many of these interactions to HCV biology remains to be determined, but it is increasingly clear that NS5A is a dynamic manipulator of the viral replicase and host cell, with potentially far reaching consequences. At present, however, a more complete understanding of NS5A in these processes is hampered by the lack of a proven function for NS5A.

SUMMARY OF THE INVENTION

The invention provides, in one embodiment, a crystallized N-terminal domain of an NS5A protein of hepatitis C virus, wherein the crystal effectively diffracts X-rays for the determination of the atomic coordinates of the domain to a resolution of greater than 5.0 Angstroms, and wherein said crystal has a space group of $P4_1 22$, with unit cell dimensions of a,b=55.28 Å, c=312.30 Å and $\alpha,\beta,\gamma=90°$.

In another embodiment, the invention provides a computer readable data storage material encoded with computer readable data comprising structure coordinates of Table 1.

In another embodiment, this invention provides a crystallized N-terminal domain of an NS5A protein of hepatitis C virus, wherein the N-terminal domain of an NS5A protein of hepatitis C virus has secondary structural elements that include 3 beta strands and an alpha helix in the N-terminal subdomain, designated as strands b1, b2, b3 and alpha helix H2 and 6 beta strands in the C-terminal subdomain, designated as b4, b5, b6, b7, b8 and b9.

In another embodiment, this invention provides a crystallized N-terminal domain of an NS5A protein of hepatitis C virus in complex with a zinc atom, wherein the zinc atom is stabilized by cysteine residues located at positions 39, 57, 59 and 80 of said protein.

In another embodiment, this invention provides a crystallized N-terminal domain of an NS5A protein of hepatitis C virus, wherein the crystallized protein is a dimer, which, in another embodiment comprises a molecular interaction surface, which, in another embodiment, comprises an isoleucine at position 90, a tryptophan at position 111, a proline at position 141, a gulatmine at position 143, a proline at position 145, a histidine at position 159, a glycine at position 178, a proline at position 192, a glutamate at position 193 of the NS5A protein, or a combination thereof.

In another embodiment, the invention provides a method of using a crystal of this invention in an inhibitor screening assay, the method comprising selecting a potential inhibitor by performing rational drug design with the three-dimensional structure determined for the crystal, wherein selecting is performed in conjunction with computer modeling, contacting the potential inhibitor with an N-terminal domain of an NS5A protein of hepatitis C virus and detecting the ability of the potential inhibitor for inhibiting infection or replication of a hepatitis C virus.

According to this aspect of the invention, and in one embodiment, the inhibitor interferes with zinc binding to the N-terminal domain of an NS5A protein. In another embodiment, the inhibitor interferes with disulfide bridge formation between cysteine residues at positions 142 and 190 of said N-terminal domain of an NS5A protein. In another embodiment, the inhibitor interferes with dimerization of NS5A proteins of the virus. In another embodiment, the inhibitor interferes with the formation of a groove between two subdomain IB regions of N-terminal domains of dimerized NS5A. In another embodiment, the inhibitor is positioned within a groove formed between two subdomain IB regions of N-terminal domains of dimerized NS5A.

In another embodiment, this invention provides a method of growing a crystallized N-terminal domain of an NS5A protein, comprising growing the crystal by vapor diffusion using a reservoir buffer containing 100 mM HEPES pH 7.0, 0.6 M trisodium citrate dihydrate, and 13% (v/v) isopropanol, at 4° C.

In another embodiment, this invention provides a method for identifying a test compound that inhibits or prevents hepatitis C viral infection or pathogenesis, the method comprising:
  a) contacting a cell infected with a hepatitis C virus in culture with a test compound, under conditions and for a time sufficient to permit the dimerization of NS5A proteins of said virus;
  b) culturing a cell infected with hepatitis virus C virus in the absence of said agent, under conditions and for a time sufficient to permit the dimerization of said NS5A protein; and
  c) comparing viral infection or pathogenic effects on cells cultured in (a) versus (b),
    whereby a decrease or absence of viral infection or pathogenic effects on cells detected in (a) as compared to (b) indicates that the test compound inhibits or prevents hepatitis C viral infection or pathogenesis.

In another embodiment, this invention provides a method for identifying a test compound that interferes with the interaction between an N-terminal domain of an NS5A protein and zinc, the method comprising:
  (a) contacting an N-terminal domain of an NS5A protein, or a fragment thereof comprising cysteine residues involved in binding a zinc ion with a zinc source, and a test compound, under conditions and for a time sufficient to permit the formation of a complex between said N-terminal domain of an NS5A protein or fragment thereof and said zinc;
  (b) an N-terminal domain of an NS5A protein, or a fragment thereof comprising cysteine residues involved in binding a zinc ion with a zinc source, and no test compound, under conditions and for a time sufficient to permit the formation of a complex between said N-terminal domain of an NS5A protein, or a fragment thereof and said zinc;
  (c) detecting the presence of a complex in (a) versus (b), whereby a decrease or absence in the complex detected in (a) as compared to (b) indicates that the test compound interferes with the interaction between an N-terminal domain of an NS5A protein and zinc.

In another embodiment, this invention provides a method for inhibiting hepatitis C viral infection or pathogenesis, comprising contacting an N-terminal domain of an NS5A protein, or a fragment thereof, of hepatitis C virus with an agent that interferes with the interaction of the NS5A protein with zinc.

In another embodiment, this invention provides a method for inhibiting hepatitis C viral infection or pathogenesis, comprising contacting an N-terminal domain of an NS5A protein, or a fragment thereof, of hepatitis C virus with an agent that inhibits or suppresses disulfide bridge formation between cysteine residues at positions 142 and 190 of said N-terminal domain of an NS5A protein.

In another embodiment, this invention provides a method for inhibiting hepatitis C viral infection or pathogenesis, comprising contacting an NS5A protein, or a fragment thereof, of hepatitis C virus with an agent that inhibits or suppresses dimerization of said NS5A protein.

In another embodiment, this invention provides a method for inhibiting hepatitis C viral infection or pathogenesis, comprising contacting an NS5A protein, or a fragment thereof, of hepatitis C virus with an agent that prevents the formation of a groove between two subdomain IB regions of N-terminal domains of dimerized NS5A.

In another embodiment, this invention provides a method for inhibiting hepatitis C viral infection or pathogenesis, comprising contacting an NS5A protein, or a fragment thereof, of hepatitis C virus with an agent that is positioned within a groove formed between two subdomain IB regions of N-terminal domains of dimerized NS5A.

In another embodiment, the methods for inhibiting hepatitis C viral infection or pathogenesis comprise preventing RNA or protein contact with residues within the groove.

BRIEF DESCRIPTION OF THE DRAWINGS

FIG. 3 demonstrates molecular surface analysis of domain I. A. Surface potential plots of the surface of domain I, with colors corresponding to acidic (black), neutral (white), and basic (grey) surfaces. Three rotations of domain I are shown, from left to right they are 'front' (FIG. 1B view), 'back' (FIG. 1C view) and 'bottom' (FIG. 1D view). The approximate rotation between images is indicated. The surface potential plots highlight the unusual 'polar' charge distribution on the surface of domain I. B. Surface of domain I colored by residue conservation, with black corresponding to 95% or greater conservation, light grey being 75-95% conservation, and white corresponding to less than 75% conservation. Domain I is presented to show the most conserved molecular surface. C. A surface potential view of the image in B is also shown. The relative positions of domain IA and IB are shown. D. A ribbon diagram view of the same orientation of domain I shown in 3C and 3D. E. Surface of domain I monomer (dark shading) with surfaces involved in dimer contacts indicated (light shading). F. Surface conservation plots as described in B, showing the conservation of the dimer interface surfaces. Dimer contacts are highlighted with a black outline.

DETAILED DESCRIPTION OF THE INVENTION

Figure 1A:
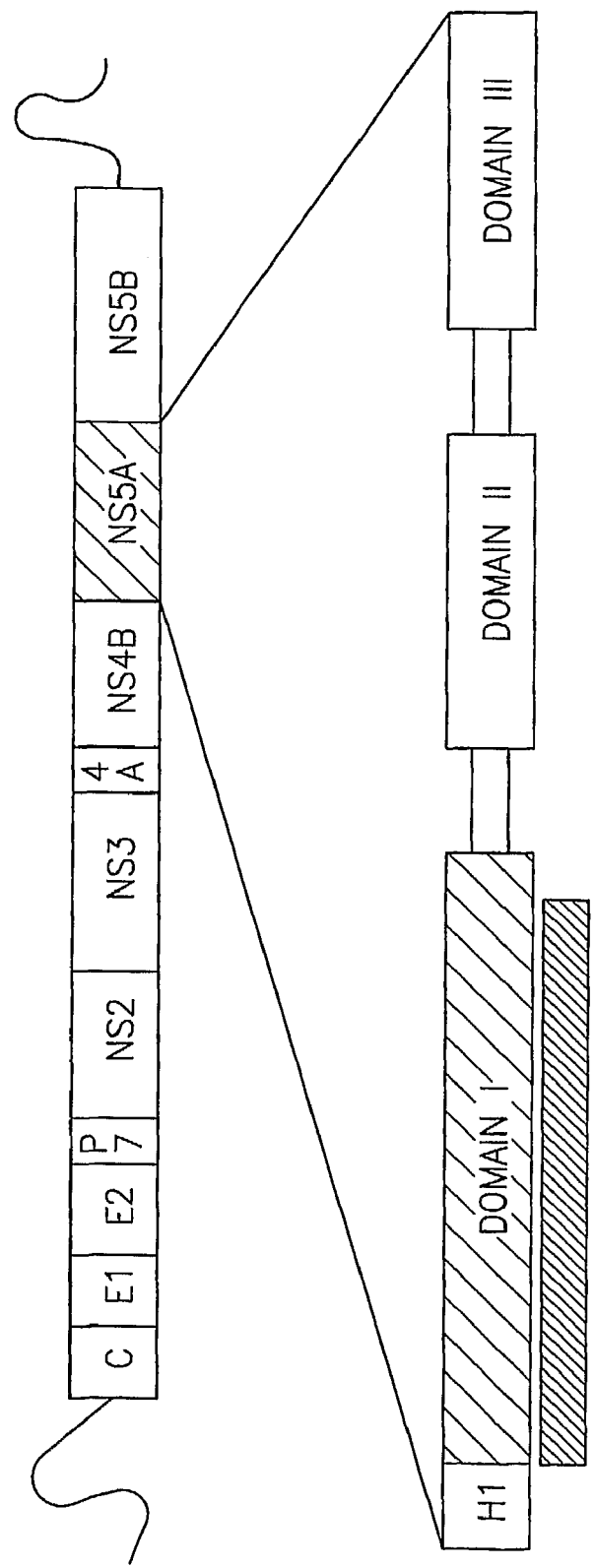
FIG. 1 schematically depicts an overview of the NS5A domain I structure. A. Schematic of HCV genome organization and domain structure of the NS5A protein. The portion of NS5A domain I observed in this structure is indicated by the staggered bar. B. Ribbon diagram of the structure of domain I. The polypeptide chain is positioned left to right, amino-terminus to carboxy-terminus. Secondary structure elements are labeled as described in the text. Domain I has been divided into two subdomains, subdomain IA and IB for ease of discussion. The single zinc atom coordinated by domain I is shown in yellow. The disulfide bond is present in subdomain IB and is circled. C. A 180° rotation showing the 'back' of domain I. D. A 45° rotation showing the 'top down' view of domain I, allowing better visualization of secondary structure elements in subdomain Ib. E. Domain I topology organization model to allow for easier tracing of the polypeptide backbone. F. Map of the pET30ubi-NS5A-Domain I-Δh plasmid.

The genome of Flaviviridae represents a single-stranded, unsegmented RNA molecule of positive polarity. Following infection and uncoating, the viral genome operates as a messenger RNA in the cytoplasm of the host cell. Translation leads to the synthesis of an unstable polyprotein that is co- and post-translationally processed by cellular as well as viral proteases to give rise to the virus structural and non-structural proteins. The structural proteins constitute the virus particle, where the virion is composed of a capsid and a membrane envelope, the latter which contains two to three membrane-associated viral envelope proteins. The non-structural proteins, which are predominantly generated by the activity of well-characterized viral proteases, are thought to act as catalytic components of the viral multiplication machinery. Virus-encoded enzymatic functions, beyond that of the viral proteases, which are essentially involved in the RNA replication process, include an RNA helicase and/or a nucleoside triphosphatase and an RNA-dependent RNA polymerase (RdRp) activity.

This invention provides, in one embodiment, crystallized N-terminal domains of a non-structural, NS5A protein of hepatitis C virus, methods of producing the same and methods of use thereof. The present invention provides, in other embodiments, structural elements of the N-terminal domain of hepatitis C virus NS5A protein, and, in other embodiments, the invention provides methods of inhibiting hepatitis C virus infection and/or pathogenesis, by interacting with, or interfering with the same.

In one embodiment, this invention provides a method of growing a crystallized N-terminal domain of an NS5A protein, comprising growing the crystal by vapor diffusion using a reservoir buffer containing 100 mM HEPES pH 7.0, 0.6 M trisodium citrate dihydrate, and 13% (v/v) isopropanol, at 4° C.

The HCV nonstructural protein NS5A is an essential replicase component that also modulates numerous cellular processes ranging from innate immunity to cell growth and survival.

NS5A has an amphipathic α-helix at its N terminus promotes association with cellular membranes, and the remainder of domain I coordinates a single zinc atom per protein molecule, where mutations disrupting either the membrane anchor or zinc binding are lethal for HCV RNA replication.

NS5A domain II and the region connecting domain I and II are hotspots for adaptive mutations that can enhance replication in cell culture by more that 10,000-fold. In addition to its role in RNA replication, NS5A antagonizes dsRNA activation of PKR and interacts with numerous cellular proteins to modulate cell growth and survival.

This invention provides, in one embodiment, a mechanistic understanding of NS5A's role in these processes.

Domain I (amino acids 36-198) has two essentially identical monomers per asymmetric unit (average r.m.s.d of 0.4 Å) packed together as a dimer via contacts near the N-terminal ends of the molecules, as exemplified herein. Domain I consists of nine β-strands (referred to as b1-b9) and a single short α-helix connected by an extensive network of extended loop regions. The helix has been designated H2, as distinguished from the N-terminal membrane anchoring helix H1. These loop regions comprise roughly 62% of the domain I structure, with a number of large (14 or more amino acids) extended random coil elements.

In another embodiment, this invention provides a crystallized N-terminal domain of an NS5A protein of hepatitis C virus, wherein the crystallized protein is a dimer, which, in another embodiment comprises a molecular interaction surface, which, in another embodiment, comprises an isoleucine at position 90, a tryptophan at position 111, a proline at position 141, a gulatmine at position 143, a proline at position 145, a histidine at position 159, a glycine at position 178, a proline at position 192, a glutamate at position 193 of the NS5A protein, or a combination thereof.

In one embodiment, the NS5A has an amino acid sequence such as that disclosed in Genbank Accession Number: AAW63112-AAW63120, AAV83498-AAV83538, NP_751927, AAS99554, AAR26038-AAR26219, AAP23306-AAP30557, AAQ75425-AAQ86584, AAK50757-AAK50761, or a sequence homologous thereto.

Crystallographic analysis was conducted herein, of the N-terminal domain of NS5A protein. The crystal form produced, is described hereinbelow.

In one embodiment, this invention provides, a crystallized N-terminal domain of an NS5A protein of hepatitis C virus, wherein the crystal effectively diffracts X-rays for the determination of the atomic coordinates of the domain to a resolution of greater than 5.0 Angstroms, and wherein said crystal has a space group of $P4_122$, with unit cell dimensions of a,b=55.28 Å, c=312.30 Å and α,β,γ=90°.

In another embodiment, the invention provides a computer readable data storage material encoded with computer readable data comprising structure coordinates of Table 1.

In another embodiment, this invention provides a crystallized N-terminal domain of an NS5A protein of hepatitis C virus, wherein the N-terminal domain of an NS5A protein of hepatitis C virus has secondary structural elements that include 3 beta strands and an alpha helix in the N-terminal subdomain, designated as strands b1, b2, b3 and alpha helix H2 and 6 beta strands in the C-terminal subdomain, designated as b4, b5, b6, b7, b8 and b9.

In another embodiment, this invention provides a crystallized N-terminal domain of an NS5A protein of hepatitis C virus in complex with a zinc atom, wherein the zinc atom is stabilized by cysteine residues located at positions 39, 57, 59 and 80 of said protein.

In another embodiment, this invention provides for the crystallization of the protein to obtain other forms, such as, having different space group and/or unit cell dimensions. In one embodiment, the structural data for the crystals of this invention may be obtained by methods known to one skilled in the art, such as those exemplified herein, and may include other structural methods such as, for example, NMR.

The crystal structure of the domain I region of NS5A, as provided herein, indicates domain I is a novel protein fold, which serves, in one embodiment, as an RNA binding groove, and/or in another embodiment, a protein binding groove, with functional implications.

The structures of the N-terminal domain of an NS5A proteins of the invention provide especially meaningful guidance for the development of drugs to target and inhibit its interaction with zinc, or in another embodiment, inhibit dimerization, or in another embodiment, inhibit groove formation, or in another embodiment, occupy the groove or otherwise render it inaccessible to protein or RNA, which, in other embodiment, represents various means to regulate NS5A activity.

Structural analysis provided an understanding of how the N-terminal domain of an NS5A protein interacts with RNA or protein. Sequence alignments of NS5A domain I regions from 30 HCV genotype reference sequences, as well as the sequence of the related GB virus B NS5A, shows the significant overall surface conservation of domain I, and highlights a large patch of conserved residues that may represent a molecular interaction surface (FIG. 3). Some of the major amino acids involved in creating this conserved surface are isoleucine 90, tryptophan 111, proline 141, gulatmine 143, proline 145, histidine 159, glycine 178, proline 192, and glutamate 193. This contiguous conserved surface spans subdomain IA and IB, including a prominent "pocket", or "groove" generated by the interface between these elements.

The dimer interface of 678 $Å^2$ consists of two patches of buried surface area, one located primarily in subdomain IA, and a second located in subdomain IB, as described further hereinbelow. The zinc-binding site is close to the interface between monomers and represents, in one embodiment, a factor involved in NS5A oligomerization.

The deep, highly basic portion of the groove has a diameter of 13.5 Å. This basic character of this groove is largely comprised of the sidechains of arginine 157, arginine 160, and lysine 44. The more hydrophobic boundary of the basic groove is considerably larger, with a diameter of 27.5 Å. The inside of the acidic arms lining the groove are separated by about 32 Å. A dsRNA molecule with a diameter of approximately 20 Å, could easily fit in the groove, making both electrostatic contacts with the deep basic groove and hydrophobic contacts with the groove boundary region. The electrostatic character of the groove is conserved among HCV sequences.

The structure coordinates provided may also be used to solve the structure of other NS5A proteins, NS5A mutants, or N-terminal domains thereof, co-complexes with the same, or of the crystalline form of any other protein with significant amino acid sequence homology thereof.

In one embodiment, crystallization of the domain I protein, can be conducted as described and exemplified herein, with crystallized products utilized in the methods of this invention, as further described. In one embodiment, the crystals of this invention may be used for compound 'soaking' in 'co-crystallization' experiments. According to this aspect of the invention, and in one embodiment, an agent of interest, such as, for example, and in one embodiment, a small molecule, may be added to the protein prior to crystallization or added to pre-formed crystals to determine the location of the binding of the small molecule on the NS5A protein by structural solution of the complex.

In one embodiment, the invention provides for a protein, or a fragment thereof, which has a structure which roughly approximates that of the domain I region of NS5A, as described herein, wherein the structure of the molecule provides for functional equivalency or correspondence with that of NS5A, such as, for example, interaction with a replicase, or, in another embodiment, host cell proteins, as described hereinbelow, or, in another embodiment, RNA. In another embodiment, the protein with similar structural characteristics will have a homologous amino acid sequence to that of the N-terminal domain of NS5A, as described hereinbelow.

In another embodiment, the invention provides for crystals which include crystallized mutants of NS5A, wherein, in one embodiment, the mutation results in abrogation of zinc incorporation, as described herein, by cysteine residues at positions 39, 57, 59, and 80.

In another embodiment, the invention provides for proteins, or in another embodiment, crystallized forms, wherein the protein comprises mutations, which result in the abrogation of disulfide bridge formation, between cysteine residues 142 and 190. In another embodiment, the mutation results in a linkage which is permanently in effect, or in another embodiment, a linkage which never forms. Such a mutation may be at a site distal to the cysteine residues, in one embodiment, such that the overall structure is altered to produce changes in terms of the nature and longevity of the linkage. It is to be understood that any protein, or fragment thereof, or crystallized form thereof, comprising such a mutation, resulting in the changing of the nature of the disulfide linkage as herein described, is to be considered as part of this invention, and applicable in the methods of this invention, as well.

In another embodiment, mutations may result in improper or lack of formation of the novel groove as described herein, which, in another embodiment, results in an alteration of the accommodation of a protein or RNA within the groove.

In one embodiment such mutated proteins, or fragments thereof, or crystallized forms thereof, may comprise mutations such that the groove is not formed, or the spacing within the groove is altered, in another embodiment, or in another embodiment, the groove is occupied, such that the protein or RNA are physically constrained from interaction as would occur with a wildtype version of the protein. In another embodiment, the mutation results in an irreversible interaction of the protein or RNA with the groove, such that the interaction is irreversible. In another embodiment, the mutation results in a changing of the nature of the residues which form the groove, such that the basic/acidic residue disposition within the groove is altered, which, in another embodiment, alters the interactions with the groove.

It is to be understood that any protein, or fragment thereof, or crystallized form thereof, comprising such a mutation, resulting in the changing of the nature of the groove as herein described, is to be considered as part of this invention, and applicable in the methods of this invention, as well.

One embodiment for a method that may be employed for such purposes, in preparing such mutated forms of the NS5A protein, or fragments thereof, is molecular replacement. In this method, in one embodiment, an unknown crystal structure may be determined using the protein structure coordinates of the N-terminal domain of NS5A of this invention.

In one embodiment, the term "molecular replacement" refers to a method that involves generating a preliminary model of a crystal of, in one embodiment, an RNA binding protein, or in another embodiment, a viral protein thought to interact with a cellular protein, whose structure coordinates are unknown, by orienting and positioning a molecule whose structure coordinates are known, such as the N-terminal domain of NS5A coordinates, within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal, as is known by those of ordinary skill in the art. Using the structure coordinates of the N-terminal domain of NS5A provided by this invention, molecular replacement can thus be used to determine the structure coordinates of, in other embodiments, a crystalline mutant or homologue of NS5A, or additional crystal forms of NS5A.

In another embodiment, the invention provides a method of using a crystal of this invention in an inhibitor screening assay, the method comprising selecting a potential inhibitor by performing rational drug design with the three-dimensional structure determined for the crystal, wherein selecting is performed in conjunction with computer modeling, contacting the potential inhibitor with an NS5A protein of hepatitis C virus and detecting the ability of the potential inhibitor for inhibiting infection or replication of a hepatitis C virus.

According to this aspect of the invention, and in one embodiment, the inhibitor interferes with zinc binding to the N-terminal domain of an NS5A protein. In another embodiment, the inhibitor interferes with disulfide bridge formation between cysteine residues at positions 142 and 190 of said N-terminal domain of an NS5A protein. In another embodiment, the inhibitor interferes with dimerization of NS5A proteins of the virus. In another embodiment, the inhibitor interferes with the formation of a groove between two subdomain IB regions of N-terminal domains of dimerized NS5A. In another embodiment, the inhibitor is positioned within a groove formed between two subdomain IB regions of N-terminal domains of dimerized NS5A.

In one embodiment, the potential inhibitor is contacted with an N-terminal domain of an NS5A protein of hepatitis C virus.

Numerous computer programs are available and suitable for rational drug design and the processes of computer modeling, model building, and computationally identifying, selecting and evaluating potential inhibitors of dimerized NS5A proteins, or N-terminal domains thereof, of hepatitis C virus in the methods described herein, and represent embodiments of this invention. These include, for example, GRID (available form Oxford University, UK), MCSS (available from Molecular Simulations Inc., Burlington, Mass.), AUTODOCK (available from Oxford Molecular Group), FLEX X (available from Tripos, St. Louis. Mo.), DOCK (available from University of California, San Francisco), CAVEAT (available from University of California, Berkeley), HOOK (available from Molecular Simulations Inc., Burlington, Mass.), and 3D database systems such as MACCS-3D (available from MDL Information Systems, San Leandro, Calif.), and UNITY (available from Tripos, St. Louis. Mo.). Potential agents may also be computationally designed "de novo" using such software packages as LUDI (available from Biosym Technologies, San Diego, Calif.), LEGEND (available from Molecular Simulations Inc., Burlington, Mass.), and LEAPFROG (Tripos Associates, St. Louis, Mo.). Compound deformation energy and electrostatic repulsion, may be evaluated using programs such as GAUSSIAN 92, AMBER, QUANTA/CHARMM, AND INSIGHT II/DISCOVER. These computer evaluation and modeling techniques may be performed on any suitable hardware including for example, workstations available from Silicon Graphics, Sun Microsystems, and the like. Any such use, as pertains to the present invention is to be considered an embodiment thereof. These techniques, methods, hardware and software packages are representative and are not intended to be comprehensive listing, and any such use represents an embodiment of the invention. Other modeling techniques known in the art may also be employed in accordance with this invention. See for example, N. C. Cohen, Molecular Modeling in Drug Design, Academic Press (1996) (and references therein), and software identified at internet sites including the CMBI Cheminformatics Suite at cheminf.cmbi.ru.nl/news/chemnews_his.shtml (Feb. 27, 2006), and the NIH Molecular Modeling Home Page at world wide web at fi.muni.cz/usr/mejzlik/mirrors/molbio.info.nih.gov/modeling/software list/ (Feb. 27, 2006). Similarly, the invention provides a computer readable data storage material encoded with computer readable data comprising structure coordinates of Table 1, and any use of the data of Table 1, is to be considered as part of this invention. It is to be understood that computer programs utilizing the structural information of this invention, or servers, or databases, comprising or utilizing the structural information of this invention, or any other means whereby the structural information may be stored in electronic format, or utilized for any purpose, including the methods of this invention, are to be considered as part of this invention.

The agent is selected by performing rational drug design with the three-dimensional structure (or structures) determined for the crystal described herein, especially in conjunction with computer modeling and methods described above. The agent is then obtained from commercial sources or is synthesized from readily available starting materials using standard synthetic techniques and methodologies known to those of ordinary skill in the art. The agent is then assayed, in one embodiment, to determine its ability to inhibit dimerization of an NS5A protein, or an N-terminal domain thereof of hepatitis C virus, or, in another embodiment, zinc association with an N-terminal domain of an NS5A protein, or in another embodiment, NS5A protein association with cellular proteins, or in another embodiment, RNA, by methods well known in the art.

The agent selected or identified by the aforementioned process may be assayed to determine its ability to affect HCV infection, in one embodiment, or in another embodiment, HCV replication. The assay may be in vitro or in vivo. The compounds described herein may be used in assays, including radiolabelled, antibody detection and fluorometric, in another embodiment, for the isolation, identification, or structural or functional characterization of NS5A. Such assays may include, in another embodiment, an assay, utilizing a full length NS5A, or in another embodiment, an N-terminal fragment thereof, which, in another embodiment, is contacted with the agent and a measurement of the binding affinity of the agent against a standard is determined.

The assay may, according to this aspect of the invention, employ fluorescence polarization measurements. Agents, such as, in one embodiment, peptides or in another embodiment, proteins, or in another embodiment, RNA, which are expected to bind to NS5A are labeled with fluorescein. Labeled agent, or in another embodiment, peptide, or in another embodiment, protein, or in another embodiment, RNA is then titrated with increasing concentrations of NS5A, and the fluorescence polarization emitted by the labeled agent/peptide is determined. Fluorescence emission polarization is proportional to the rotational correlation time (tumbling) of the labeled molecule. Tumbling, in part, depends on the molecular volume, i.e. larger molecules have larger volume and slower tumbling which in turn gives rise to increased polarization of emitted light. If the agent/peptide associates with NS5A, its effective molecular volume greatly increases, which may be evidenced by values obtained for polarization fluorescence emissions.

In one embodiment, complexes of peptides, or in another embodiment, proteins, or in another embodiment, RNA, or in another embodiment, agents, with the N-terminal domain of an NS5A protein may be studied using well-known X-ray diffraction techniques, or in another embodiment, as exemplified herein, and in another embodiment, may be refined versus 2-3 angstrom resolution X-ray data to an R value of about 0.20 or less using readily available computer software, such as X-PLOR (Yale University©, 1992, distributed by Molecular Simulations, Inc.; Blundel & Johnson, 1985, specifically incorporated herein by reference).

The design of compounds that inhibit NS5A protein dimerization, or that of N-terminal domains thereof and/or, in another embodiment, protein activity, according to this invention may involve several considerations. In one embodiment, the compound should be capable of physically and structurally associating with the N-terminal domain of an NS5A protein, such as, in other embodiments, by using non-covalent molecular interactions, including hydrogen bonding, van der Waals and hydrophobic interactions and the like. In another embodiment, the compound may assume a conformation that allows it to associate with the N-terminal domain of an NS5A protein, or in another embodiment, with the zinc binding region, or in another embodiment, with regions important in groove formation. In another embodiment, although certain portions of the compound may not directly participate in this association with NS5A, those portions may still influence the overall conformation of the molecule, or in another embodiment, with formation of the groove, or in another embodiment, with exposure of regions of the groove to protein, or RNA, or in another embodiment, to zinc binding. This, in turn, may have a significant impact on potency. Such conformational requirements include the overall three-dimensional structure and orientation of the chemical entity or compound in relation to all or a portion of the binding site, in another embodiment.

In another embodiment, an inhibitor may be designed using the structure of domain I, where the inhibitors disrupt inter-subdomain contacts in NS5A. In one embodiment, molecules are designed to specifically bind at the interface between the sub-domain IA and sub-domain 1B regions of the protein and inhibit function by altering molecular conformation. In another embodiment, an inhibitor is designed using the basic membrane interaction surface identified in the structure of domain I.

In one embodiment, the term "inhibitor" refers to a molecule which affects NS5A structure, and/or, in another embodiment, function and/or, in another embodiment, activity. In one embodiment, the inhibitors obtained via this invention may also be referred to as "drugs", in that they may be administered to a subject as part of anti-viral therapy.

The potential inhibitory activity of a chemical compound on NS5A dimerization and/or activity may be analyzed prior to its actual synthesis and testing by the use of computer modeling techniques, as is known to those of ordinary skill in the art.

One of ordinary skill in the art may use, in other embodiments of this invention, any one of several methods to screen chemical entities or fragments for their ability to associate with NS5A, or an N-terminal domain thereof, and, in another embodiment, with the zinc binding site of NS5A. This process may begin by visual inspection of, for example, the zinc binding site of NS5A on the computer screen based on data presented in, for example, FIG. 2, or with the groove, etc.

Selected fragments or chemical entities may then be positioned in a variety of orientations, or docked, within the zinc binding site, or within the groove formed in dimerized N-terminal domains of the NS5A proteins, for example, and in other embodiments. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include, in one embodiment, the programs GRID, MCSS, AUTODOCK and DOCK.

Once suitable chemical entities or fragments have been selected, they may, in another embodiment, be assembled into a single compound. Assembly may be preceded by visual inspection of the relationship of the fragments to each other on the three-dimensional image displayed on a computer screen in relation to the structure coordinates of NS5A protein. This may be followed, in another embodiment, by manual model building using software such as Quanta or Sybyl.

Useful programs to aid one of skill in the art in connecting the individual chemical entities or fragments include, in other embodiments, CAVEAT, 3D Database systems such as MACCS-3D (MDL Information Systems, San Leandro, Calif.) and HOOK.

In another embodiment, instead of proceeding to build an agent which interacts with the NS5A protein, or an N-terminal fragment thereof, in a step-wise fashion, one fragment or chemical entity at a time as described above, the agent may be designed as a whole or "de novo" using either an empty binding site. These methods may include the use of programs such as LUDI, LEGEND and LeapFrog, each of which represents an embodiment of this invention.

In another embodiment, once a compound has been designed or selected by the above methods, the efficiency with which that compound may bind to the NS5A protein may be tested and optimized by computational evaluation. In such methods, the deformation energy of binding may be considered and agents, which interact with the NS5A protein, or an N-terminal fragment thereof, may be designed with a particular deformation energy of binding, as will be understood by one of ordinary skill in the art.

A compound designed or selected as binding to the NS5A protein may, in another embodiment, be further computationally optimized so that in its bound state it would preferably lack repulsive electrostatic interaction with the NS5A protein. Such non-complementary (e.g., electrostatic) interactions include, in other embodiments, repulsive charge-charge, dipole-dipole and charge-dipole interactions. Specifically, the sum of all electrostatic interactions between the bound agent and the NS5A protein, make, in another embodiment, a neutral or favorable contribution to the enthalpy of binding.

Specific computer software is available in the art to evaluate compound deformation energy and electrostatic interaction, and may include, in other embodiments, Gaussian 92, revision C (Frisch, Gaussian, Inc., Pittsburgh, Pa.,© 1992); AMBER, version 4.0 (Kollman, University of California at San Francisco, (1994); QUANTA/CHARMM (Molecular Simulations, Inc., Burlington, Mass., 1994); or Insight II/Discover (Biosym Technologies Inc., San Diego, Calif.,© 1994).

In another embodiment, once an agent binding to a NS5A protein, or an N-terminal fragment thereof, has been optimally selected or designed, as described above, substitutions may then be made in some of its atoms or side groups in order to improve or modify its binding properties. In one embodiment, initial substitutions are conservative, i.e., the replacement group will have approximately the same size, shape, hydrophobicity and charge as the original group. Such substituted chemical compounds may then be, in another embodiment, analyzed for efficiency of fit to the NS5A protein, or an N-terminal fragment thereof by the same computer methods described in detail, above.

In another embodiment, the agent interferes with the formation of a groove in dimerized NS5A, or in another embodiment, occupies the groove, such that no other molecule may be accommodated within the groove, thereby inhibiting NS5A activity. In one embodiment, the agent constrains the N-terminus of the protein, or in another embodiment, the agent prevents the orientation of the groove in facing away from the cell membrane. In another embodiment, the agent provides steric hindrace such that the physical organization of the groove is diminished or absent.

In one embodiment, the agent is an antibody.

In one embodiment, the term "antibody" refers to intact molecules as well as functional fragments thereof, such as Fab, F(ab')$_2$, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')$_2$, refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art. (See for example, Harlow and Lane, Antibodies: A Laboratory Manual, Cold Spring Harbor Laboratory, New York, 1988, incorporated herein by reference).

Antibody fragments for use according to the methods of the present invention can be prepared, in one embodiment, through proteolytic hydrolysis of an appropriate antibody, or, in other embodiments, by expression in *E. coli* or mammalian cells (e.g. Chinese hamster ovary cell culture or other protein expression systems) of DNA encoding the fragment.

In some embodiments, antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. In other embodiments, enzymatic cleavage using pepsin can be used to produce two monovalent Fab' fragments and an Fc fragment directly. These methods are described, for example, by Goldenberg, U.S. Pat. Nos. 4,036, 945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, in some embodiments, as described in Inbar et al., Proc. Nat'l Acad. Sci. USA 69:2659-62, 1972. In other embodiments, the variable chains can be linked by an intermolecular disulfide bond or cross-linked by chemicals such as glutaraldehyde. In some embodiments, the Fv fragments comprise VH and VL chains connected by a peptide linker. These single-chain antigen binding proteins (sFv) may be prepared by constructing a structural gene comprising DNA sequences encoding the VH and VL domains connected by an oligonucleotide. The structural gene may be inserted into an expression vector, which is subsequently introduced into a host cell such as E. coli. The recombinant host cells may synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11: 1271-77, 1993; and Ladner et al., U.S. Pat. No. 4,946,778, which are hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In another embodiment, the agent is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

It is to be understood that any compound, such as a crystal, protein or peptide comprising, or derived from an N-terminal domain of NS5A, for any use in this invention may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In other embodiments, the crystal or peptide comprising, or derived from an N-terminal domain of NS5A of the present invention may be employed in the following applications: 1) screening assays; 2) predictive medicine (e.g., diagnostic assays, prognostic assays, monitoring clinical trials, and pharmacogenetics); and 3) methods of treatment (e.g., therapeutic and prophylactic).

In one embodiment, this invention provides a method for identifying a test compound that inhibits or prevents hepatitis C viral infection or pathogenesis, the method comprising:
(a) contacting a cell infected with a hepatitis C virus in culture with a test compound, under conditions and for a time sufficient to permit the dimerization of NS5A proteins of said virus;
(b) culturing a cell infected with hepatitis virus C virus in the absence of said agent, under conditions and for a time sufficient to permit the dimerization of said NS5A protein; and
(c) comparing viral infection or pathogenic effects on cells cultured in (a) versus (b),
whereby a decrease or absence of viral infection or pathogenic effects on cells detected in (a) as compared to (b) indicates that the test compound inhibits or prevents hepatitis C viral infection or pathogenesis.

In another embodiment, this invention provides a method for identifying a test compound that inhibits the interaction between an N-terminal domain of an NS5A protein and zinc, the method comprising:
(a) contacting an N-terminal domain of an NS5A protein, or a fragment thereof comprising cysteine residues involved in binding a zinc ion with a zinc source, and a test compound, under conditions and for a time sufficient to permit the formation of a complex between said N-terminal domain of an NS5A protein or fragment thereof and said zinc;
(b) an N-terminal domain of an NS5A protein, or a fragment thereof comprising cysteine residues involved in binding a zinc ion with a zinc source, and no test compound, under conditions and for a time sufficient to permit the formation of a complex between said N-terminal domain of an NS5A protein, or a fragment thereof and said zinc;
(c) detecting the presence of a complex in (a) versus (b), whereby a decrease or absence in the complex detected in (a) as compared to (b) indicates that the test compound inhibits the interaction between an N-terminal domain of an NS5A protein and zinc.

In one embodiment, the binding site for zinc comprises a cysteine residue at positions 39, 57, 59, 80 or combinations thereof.

In one embodiment, the compound identified in the screening methods as described, may be identified by computer modeling techniques, and others, as described hereinabove. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In one embodiment, the test compound identified by the methods of this invention, as inhibiting HCV infection, or in another embodiment, replication, or in another embodiment, pathogenesis, or in another embodiment, a combination thereof, may effect this activity via its prevention, diminution or abrogation of zinc binding to an HCV NS5A protein, or in another embodiment, disulfide bridge formation, as described, or in another embodiment, groove formation, or in another embodiment, a combination thereof. Such a compound thus identified may be used in other embodiments as part of the methods of this invention, for inhibiting HCV infection, or in another embodiment, replication, or in another embodiment, pathogenesis. In other embodiments, the test compounds thus identified, compositions comprising the test compounds, crystallized forms, etc., are to be considered as part of this invention and embodiments thereof. Optimized forms of such compounds may be generated, by methods as will be appreciated by those of skill in the art, which may enhance interactions of key positions within the test compounds and residues within HCV NS5A proteins, and represent embodiments of this invention.

In another embodiment, this invention provides a method for inhibiting Hepatitis C viral infection or pathogenesis, comprising contacting an N-terminal domain of an NS5A protein, or a fragment thereof, of hepatitis C virus with an agent that inhibits or suppresses the interaction of the NS5A protein with zinc.

In another embodiment, this invention provides a method for inhibiting hepatitis C viral infection or pathogenesis, comprising contacting an N-terminal domain of an NS5A protein, or a fragment thereof, of hepatitis C virus with an agent that inhibits or suppresses disulfide bridge formation between cysteine residues at positions 142 and 190 of said N-terminal domain of an NS5A protein.

Figure 5:
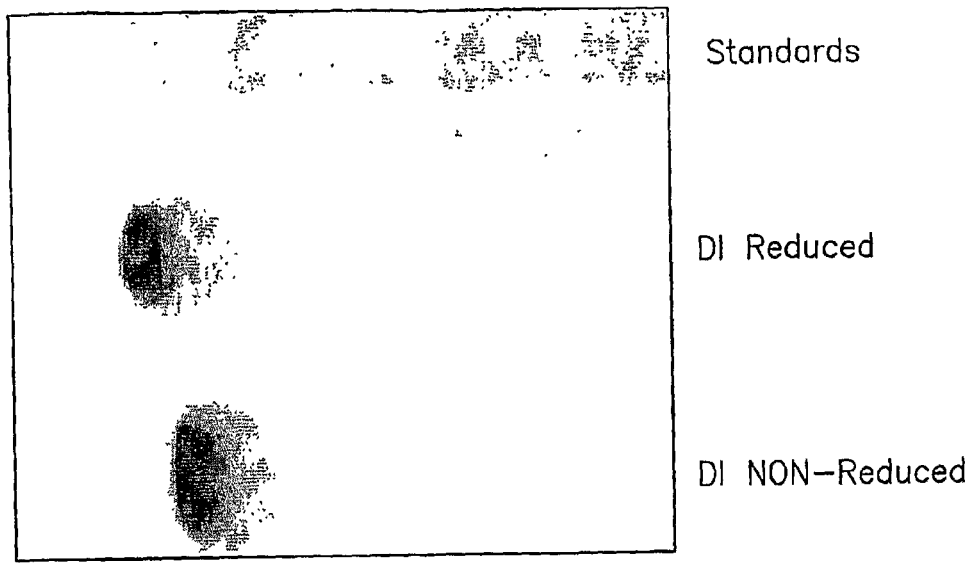
FIG. 5 shows the altered electrophoretic mobility of the NS5A domain I under reducing and non-reducing conditions in sodium dodecyl sulfate polyacrylamide gel electrophoresis. The lane labeled standard corresponds to protein size standards used as a control for mobility. The lane labeled DI Reduced corresponds to NS5A domain I treated with the reducing agent dithiothreitol prior to electrophoresis. The lane labeled DI Non-Reduced corresponds to NS5A domain I that was not treated with reducing agent. Note the difference in mobility between NS5A domain I in these two lanes, suggesting the presence of a disulfide bond in this protein.

NS5A dimerization was shown, for example, in FIG. 5. In another embodiment, this invention provides a method for inhibiting hepatitis C viral infection or pathogenesis, comprising contacting an NS5A protein, or a fragment thereof, of hepatitis C virus with an agent that inhibits or suppresses dimerization of said NS5A protein.

In another embodiment, this invention provides a method for inhibiting hepatitis C viral infection or pathogenesis, comprising contacting an NS5A protein, or a fragment thereof, of hepatitis C virus with an agent that prevents the formation of a groove between two domain IB regions of N-terminal domains of dimerized NS5A.

In another embodiment, this invention provides a method for inhibiting hepatitis C viral infection or pathogenesis, comprising contacting an NS5A protein, or a fragment thereof, of hepatitis C virus with an agent that is positioned within a groove formed between two domain IB regions of N-terminal domains of dimerized NS5A.

In another embodiment, the methods for inhibiting hepatitis C viral infection or pathogenesis comprise preventing RNA or protein contact with residues within the groove. For example, as shown herein, preferential single stranded RNA contact with NS5A was shown.

In another embodiment, any method of inhibiting hepatitis C viral infection or pathogenesis may further comprise the administration of an interferon, such as, for example, Intron-A (interferon alpha-2b) by Schering, PEG-INTRON (pegylated interferon alpha-2b) by Schering, Roferon-A (interferon alfa-2a) by Roche, PEGASYS (pegylated interferon alfa-2a) by Roche, INFERGEN (interferon alfacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and Interferon gamma-1b by InterMune.

In another embodiment, any method of inhibiting hepatitis C viral infection and/or replication and/or pathogenesis may further comprise the administration of nucleoside analogs, such as, for example, synthetic guanosine analogs, such as, for example, ribavirin.

In another embodiment, the method of inhibiting hepatitis C viral infection or pathogenesis may comprise the administration of a crystallized N-terminal domain of an NS5A protein, or a mutated version thereof, wherein the protein serves to interfere with dimer formation, in one embodiment, such that the fragment dimerizes with an HCV NS5A protein expressed in an infected cell, such that functional dimer formation is prevented. In one embodiment, the mutated NS5A protein results in improper formation of the groove, or in another embodiment, occupation of the groove such that the NS5A protein cannot interact with cellular proteins or RNA, thereby inhibiting hepatitis C viral infection or pathogenesis.

In another embodiment, the structure, and in another embodiment, function of NS5A proteins, and in another embodiment, N-terminal domains thereof, is conserved among other Flaviviridae. According to this aspect of the invention, and in another embodiment, methods of this invention utilizing the N-terminal domain of HCV NS5A protein are applicable to other Flaviviridae. In one embodiment, screening methods utilizing HCV N-terminal domains of NS5A protein may be utilized for identifying inhibitors of other Flaviviridae, or in another embodiment, N-terminal domains of NS5A protein of the respective Flaviviridae may be used.

In one embodiment, the N-terminal domains of Flaviviridae NS5A protein have a sequence such as that disclosed in Genbank Accession Number: NP_776270, NP_803208, AAS45125-AAS45130, NP_777518, NP_777531, NP_757360, or one homologous thereto.

In one embodiment, the terms "homology", "homologue" or "homologous", refer to a molecule, which exhibits, in one embodiment at least 70% correspondence with the indicated molecule, in terms of, in one embodiment, its structure, or in another embodiment, amino acid sequence. In another embodiment, the molecule exhibits at least 72% correspondence with the indicated sequence or structure. In another embodiment, the molecule exhibits at least 75% correspondence with the indicated sequence or structure. In another embodiment, the molecule exhibits at least 80% correspondence with the indicated sequence or structure. In another embodiment, the molecule exhibits at least 82% correspondence with the indicated sequence or structure. In another embodiment, the molecule exhibits at least 85% correspondence with the indicated sequence or structure. In another embodiment, the molecule exhibits at least 87% correspondence with the indicated sequence or structure. In another embodiment, the molecule exhibits at least 90% correspondence with the indicated sequence or structure. In another embodiment, the molecule exhibits at least 92% correspondence with the indicated sequence or structure. In another embodiment, the molecule exhibits at least 95% or more correspondence with the indicated sequence or structure. In another embodiment, the molecule exhibits at least 97% correspondence with the indicated sequence or structure. In another embodiment, the molecule exhibits at least 99% correspondence with the indicated sequence or structure. In another embodiment, the molecule exhibits 95%-100% correspondence with the indicated sequence or structure. Similarly, as used herein, the reference to a correspondence to a particular molecule includes both direct correspondence, as well as homology to that molecule as herein defined.

Homology, as used herein, may refer to sequence identity, or may refer to structural identity, or functional identity. By using the term "homology" and other like forms, it is to be understood that any molecule, that functions similarly, and/or contains sequence identity, and/or is conserved structurally so that it approximates the reference molecule, is to be considered as part of this invention.

In one embodiment, determining inhibition of HCV replication and/or infection and/or pathogenesis may be accomplished via incubating the test compound, or in another embodiment, the agent, or in another embodiment, a crystal of this invention, in a medium with a liver slice prepared from a subject having hepatitis for a period of time, e.g., 24 to 96 hours, and then determining the replication level of the virus, such as genome level, protein level, or the replication rate of the virus, in the liver slice. One may also determine a control replication level of the virus in a second liver slice in the same manner except that the second liver slice is incubated in a medium free of the compound. If the replication level in the first slice is lower than that in the second slice, the compound is to be considered as inhibiting HCV replication and/or infection and/or pathogenesis.

A liver slice can be prepared using techniques well known in the art. It can be prepared in different dimensions and maintained in various culture systems. See, e.g., Groneberg et al., Toxicol. Pathol. 30 (2002) 394-399 and Ekins Drug Metab. Rev. 28 (1996) 591-623. A plurality of liver slices can be obtained from a subject and stored in, e.g., liquid nitrogen, for later use (Isacheako et al., Eur. J. Obstet. Gynecol. Reprod. Biol. 2003 Jun. 10; 108(2):186-93). These slices can also be used in parallel to screen different compounds, thereby achieving high-throughput screening.

The replication level of a virus can be determined, in other embodiments, using techniques known in the art. For example, the genome level can be determined using RT-PCR. To determine the level of a viral protein, one can use techniques including ELISA, immunoprecipitation, immunofluorescence, EIA, RIA, and Western blotting analysis. To determine the replication rate of a virus, one can use the method described in, e.g., Billaus et al., Virology 26 (2000) 180-188.

In another embodiment, determining inhibition of HCV replication and/or infection and/or pathogenesis may be accomplished via determining a responsiveness of a subject to an agent, or in another embodiment, a test compound identified via the methods of this invention, or in another embodiment, a crystal of this invention.

To evaluate a subject's responsiveness to such materials, in one embodiment, a number of liver slices from the subject are prepared, and the slices are incubated with the materials, respectively. A replication level of the virus in each of the liver slices is determined, and compared to a control level in the manner described above, in one embodiment. The subject is determined to be responsive to the material if the replication level in a slice incubated with the material is lower than the control level.

This method can be used, in other embodiments, as a means of monitoring hepatitis treatment in a subject. For this purpose, liver slices may be prepared from a subject before, during, and after undergoing treatment. The slices are then subjected to the treatment in vitro, and the replication level of the virus in each slice is obtained in the manner described above.

In another embodiment, the inhibition of HCV replication and/or infection and/or pathogenesis includes inhibition of downstream effects of HCV or infection with other Flaviviridae. In one embodiment, downstream effects include neoplastic disease, including, in one embodiment, the development of hepatocellular carcinoma.

In one embodiment, the molecular architecture of the dimerized N-terminal domains of the NS5A supports, and in another embodiment, maximizes protein-protein interactions with other proteins. Proteins that associate with the domain may comprise, in one embodiment, kinases, such as, for example, IFN-activated PKR, Phosphoinositide-3-kinase p85 subunit, or in another embodiment, other cellular proteins, including, inter-alia, signaling proteins. Some examples of the cellular proteins are p53, TNFR-associated factor 2 (TRAF2), Karyopherin 3, Apolipoprotein A1, Homeodomain protein PTX1, hTAFII32 (component of TFIID) the La autoantigen, and others. According to this aspect of the invention, NS5A may serve as a nexus of the signaling pathways tied to HCV pathogenesis and represents, in another embodiment of this invention, an effective target for multiple clinically relevant scenarios, as will be appreciated by one skilled in the art.

In another embodiment, protein, or in another embodiment, peptide or in another embodiment, other inhibitors of the present invention cause inhibition of infection, replication, or pathogenesis of hepatitis C Virus in vitro or, in another embodiment, in vivo when introduced into a host cell containing the virus, and may exhibit, in another embodiment, an IC50 in the range of from about 0.0001 nM to 100 μM in an in vitro assay for at least one step in infection, replication, or pathogenesis of HCV, more preferably from about 0.0001 nM to 75 μM, more preferably from about 0.0001 nM to 50 μM, more preferably from about 0.0001 nM to 25 μM, more preferably from about 0.0001 nM to 10 μM, and even more preferably from about 0.0001 nM to 1 μM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology indicates a lack of HCV infection.

In another embodiment, this invention provides for compositions comprising a crystallized N-terminal domain of an NS5A protein, or a mutant thereof, or a homologue thereof, wherein the homologue exhibits significant structural or sequence homology to the NS5A protein. In another embodiment, this invention provides for compositions comprising an agent, as herein described, which inhibits hepatitis C viral infection or pathogenesis, obtained via the methods of this invention.

In one embodiment, the term "composition" refers to any such composition suitable for administration to a subject, and such compositions may comprise a pharmaceutically acceptable carrier or diluant, for any of the indications or modes of administration as described. The active materials in the compositions of this invention can be administered by any appropriate route, for example, orally, parenterally, intravenously, intradermally, subcutaneously, or topically, in liquid or solid form.

In one embodiment, the dose of the active ingredient is in the range from about 1 to 50 mg/kg, or in another embodiment, 1 to 20 mg/kg, of body weight per day, or in another embodiment, 0.1 to about 100 mg per kilogram body weight of the recipient per day. The effective dosage range of the active ingredient/s can be calculated by means known to those skilled in the art.

The active ingredient in the compositions of this invention can be conveniently administered in any suitable unit dosage form, including but not limited to one containing 7 to 3000 mg, preferably 70 to 1400 mg, of active ingredient per unit dosage form. For example, an oral dosage of 50-1000 mg of the active ingredient may be convenient.

In one embodiment, the active ingredient is administered to achieve peak plasma concentrations of from about 0.2 to 70 μM, or in another embodiment, from about 1.0 to 10 μM. This can be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In one embodiment, the mode of administration of the active compound is oral. Oral compositions may, in another embodiment, include an inert diluent or an edible carrier. They can be enclosed in gelatin capsules or compressed into tablets. In one embodiment, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active ingredient can be administered as a component of an elixir, suspension, syrup, wafer, chewing gum or the like. A syrup can contain, in addition to the active compounds, sucrose as a sweetening agent and certain preservatives, dyes and colorings and flavors.

The active ingredient may, in other embodiments, be mixed with other active materials that do not impair the desired action, or with materials that supplement the desired action, such as antibiotics, antifungals, anti-inflammatories, or other antivirals, including nucleoside inhibitors. Solutions or suspensions used for parenteral, intradermal, subcutaneous, or topical application can include, in other embodiments, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In another embodiment, compositions for intravenous administration may comprise carriers such as physiological saline or phosphate buffered saline (PBS).

In another embodiment, the active ingredients may be prepared with carriers, which protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) represent other embodiments of pharmaceutically acceptable carriers. These can be prepared according to methods known to those skilled in the art, for example, as described in U.S. Pat. No. 4,522,811, which is incorporated herein by reference in its entirety. For example, liposome formulations can be prepared by dissolving appropriate lipid(s), such as stearoyl phosphatidyl ethanolamine, stearoyl phosphatidyl choline, arachadoyl phosphatidyl choline, and/or cholesterol, in an inorganic solvent that is then evaporated, leaving behind a thin film of dried lipid on the surface of the container. An aqueous solution of the active ingredient is then introduced into the container. The container is swirled by hand to free lipid material from the sides of the container and to disperse lipid aggregates, thereby forming the liposomal suspension.

The active ingredient(s) are included in the pharmaceutically acceptable carrier or diluent in an amount sufficient to deliver to a subject a therapeutically effective amount of compound to inhibit viral replication, or infection, in vivo, especially Flaviviridae replication, without causing serious toxic effects in the treated patient. By "inhibitory amount" is meant an amount of active ingredient sufficient to exert an inhibitory effect as measured by, for example, an assay such as the ones described herein.

In one embodiment, the composition may be formulated to provide controlled delivery. In one embodiment, such a composition may comprise a biodegradable polymer such as polylactic acid (Kulkarni et al., in 1966 "Polylactic acid for surgical implants," Arch. Surg., 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and WO 97/05185 to Focal, Inc. directed to multiblock biodegradable hydrogels for use as controlled release agents for drug delivery and tissue treatment agents.

Degradable materials of biological origin, such as crosslinked gelatin, are well known, and represent other embodiments for use in compositions of this invention. Another example is hyaluronic acid, which has been crosslinked and used as a degradable swelling polymer for biomedical applications (U.S. Pat. No. 4,957,744 to Della Valle et. al.; (1991) "Surface modification of polymeric biomaterials for reduced thrombogenicity," Polym. Mater. Sci. Eng., 62:731-735]).

Many dispersion systems are currently in use, or being explored for use, as carriers of substances, and particularly of biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses yet another method for drug delivery by forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

It is to be understood that any applicable drug delivery system may be used with the compositions and/or agents/crystals of this invention, for administration to a subject, and is to be considered as part of this invention.

For example, U.S. Pat. No. 5,578,325 discloses the use of nanoparticles and microparticles of non-linear hydrophilic hydrophobic multiblock copolymers for drug delivery. U.S. Pat. No. 5,545,409 discloses a delivery system for the controlled release of bioactive factors. U.S. Pat. No. 5,494,682 discloses the use of ionically cross-linked polymeric microcapsules as a drug delivery system. U.S. Pat. No. 5,728,402 to Andrx Pharmaceuticals, Inc. describes a controlled release formulation that includes an internal phase that comprises the active drug, its salt or prodrug, in admixture with a hydrogel forming agent, and an external phase which comprises a coating that resists dissolution in the stomach. U.S. Pat. Nos. 5,736,159 and 5,558,879 to Andrx Pharmaceuticals, Inc. disclose controlled release formulations for drugs with little water solubility in which a passageway is formed in situ. U.S. Pat. No. 5,567,441 to Andrx Pharmaceuticals, Inc. discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the anti-HCV compounds, or in another embodiment, compositions of the invention will depend on the nature of the anti-HCV agent, the condition of the subject, and the judgment of the practitioner. Design of such administration and formulation is routine optimization generally carried out without difficulty by the practitioner.

The following examples are intended to illustrate but not limit the present invention.

EXAMPLES

Materials and Experimental Methods

Protein Preparation

The expression and purification of NS5A Domain I-Δh was performed as described previously (Tellinghuisen, T. L., et al. *J Biol Chem* (2004)). For the expression of NS5A-Domain I-Δh, 1 L of LB medium supplemented with 30 μg/L of kanamycin and 25 μg/L of chloramphenicol was inoculated from an overnight culture of *E. coli* BL21(de3) containing pET30ubi-NS5A-Domain I-Δh (FIG. 1F) and pCG1 plasmids such that the cell density was at approximately $OD_{600}$ of 0.05.

The Domain I protein sequence encoded in the plasmid was as follows:

```
                                              (SEQ ID NO: 1)
MQIFVKTLTGKTITLEVESSDTIDNVKSKIQDKEGIPPDQQRLIFAGKQL

EDGRTLSDYNIQKESTLHLVLRLRGGSKLLPRLPGVPFFSCQRGYKGVWR

GDGIMQTTCPCGAQITGHVKNGSMRIVGPRTCSNTWHGTFPINAYTTGPC

TPSPAPNYSRALWRVAAEEYVEVTRVGDFHYVTGMTTDNVKCPCQVPAPE

FFTEVDGVRLHRYAPACKPLLREEVTFLVGLNQYLVGSQLPCEPEPDVAV

LTSMLTDPSHITAETAKRGTDDDDKAMAISDPNSSSVDKLAAALEHHHHH

H, with the bolded characters representing the
```

-continued sequence of the ubiquitin fusion tag used for the expression system.

The domain I HCV protein sequence with a C-terminal fusion tag was as follows (underlined sequence represents the C-terminal tag):

(SEQ ID NO: 2)

SKLLPRLPGVPFFSCQRGYKGVWRGDGIMQTTCPCGAQITGHVKNGSMRI

VGPRTCSNTWHGTFPINAYTTGPCTPSPAPNYSRALWRVAAEEYVEVTRV

GDFHYVTGMTTDNVKCPCQVPAPEFFTEVDGVRLHRYAPACKPLLREEVT

FLVGLNQYLVGSQLPCEPEPDVAVLTSMLTDPSHITAETAKRGTDDDDKA

MAISDPNSSSVDKLAAALEHHHHHH.

The complete plasmid coding sequence for domain I production was as follows:

(SEQ ID NO: 3)

TGGCGAATGGGACGCGCCCTGTAGCGGCGCATTAAGCGCGGCGGGTGTGG

TGGTTACGCGCAGCGTGACCGCTACACTTGCCAGCGCCCTAGCGCCCGCT

CCTTTCGCTTTCTTCCCTTCCTTTCTCGCCACGTTCGCCGGCTTTCCCCG

TCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGG

CCATCGCCCTGATAGACGGTTTTTCGCCCTTTGACGTTGGAGTCCACGTT

CTTTAATAGTGGACTCTTGTTCCAAACTGGAACAACACTCAACCCTATCT

CGGTCTATTCTTTTGATTTATAAGGGATTTTGCCGATTTCGGCCTATTGG

TTAAAAAATGAGCTGATTTAACAAAAATTTAACGCGAATTTTAACAAAAT

ATTAACGTTTACAATTTCAGGTGGCACTTTTCGGGGAAATGTGCGCGGAA

CCCCTATTTGTTTATTTTTCTAAATACATTCAAATATGTATCCGCTCATG

AATTAATTCTTAGAAAAACTCATCGAGCATCAAATGAAACTGCAATTTAT

TCATATCAGGATTATCAATACCATATTTTTGAAAAAGCCGTTTCTGTAAT

GAAGGAGAAAACTCACCGAGGCAGTTCCATAGGATGGCAAGATCCTGGTA

TCGGTCTGCGATTCCGACTCGTCCAACATCAATACAACCTATTAATTTCC

CCTCGTCAAAAATAAGGTTATCAAGTGAGAAATCACCATGAGTGACGACT

GAATCCGGTGAGAATGGCAAAAGTTTATGCATTTCTTTCCAGACTTGTTC

AACAGGCCAGCCATTACGCTCGTCATCAAAATCACTCGCATCAACCAAAC

CGTTATTCATTCGTGATTGCGCCTGAGCGAGACGAAATACGCGATCGCTG

TTAAAAGGACAATTACAAACAGGAATCGAATGCAACCGGCGCAGGAACAC

TGCCAGCGCATCAACAATATTTTCACCTGAATCAGGATATTCTTCTAATA

CCTGGAATGCTGTTTTCCCGGGGATCGCAGTGGTGAGTAACCATGCATCA

TCAGGAGTACGGATAAAATGCTTGATGGTCGGAAGAGGCATAAATTCCGT

CAGCCAGTTTAGTCTGACCATCTCATCTGTAACATCATTGGCAACGCTAC

CTTTGCCATGTTTCAGAAACAACTCTGGCGCATCGGGCTTCCCATACAAT

CGATAGATTGTCGCACCTGATTGCCCGACATTATCGCGAGCCCATTTATA

-continued

CCCATATAAATCAGCATCCATGTTGGAATTTAATCGCGGCCTAGAGCAAG

ACGTTTCCCGTTGAATATGGCTCATAACACCCCTTGTATTACTGTTTATG

TAAGCAGACAGTTTTATTGTTCATGACCAAAATCCCTTAACGTGAGTTTT

CGTTCCACTGAGCGTCAGACCCCGTAGAAAAGATCAAAGGATCTTCTTGA

GATCCTTTTTTTCTGCGCGTAATCTGCTGCTTGCAAACAAAAAAACCACC

GCTACCAGCGGTGGTTTGTTTGCCGGATCAAGAGCTACCAACTCTTTTTC

CGAAGGTAACTGGCTTCAGCAGAGCGCAGATACCAAATACTGTCCTTCTA

GTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATA

AGTCGTGTCTTACCGGGTTGGACTCAAGACGATAGTTACCGGATAAGGCG

CAGCGGTCGGGCTGAACGGGGGGTTCGTGCACACAGCCCAGCTTGGAGCG

AACGACCTACACCGAACTGAGATACCTACAGCGTGAGCTATGAGAAAGCG

CCACGCTTCCCGAAGGGAGAAAGGCGGACAGGTATCCGGTAAGCGGCAGG

GTCGGAACAGGAGAGCGCACGAGGGAGCTTCCAGGGGGAAACGCCTGGTA

TCTTTATAGTCCTGTCGGGTTTCGCCACCTCTGACTTGAGCGTCGATTTT

TGTGATGCTCGTCAGGGGGGCGGAGCCTATGGAAAAACGCCAGCAACGCG

GCCTTTTTACGGTTCCTGGCCTTTTGCTGGCCTTTTGCTCACATGTTCTT

TCCTGCGTTATCCCCTGATTCTGTGGATAACCGTATTACCGCCTTTGAGT

GAGCTGATACCGCTCGCCGCAGCCGAACGACCGAGCGCAGCGAGTCAGTG

AGCGAGGAAGCGGAAGAGCGCCTGATGCGGTATTTTCTCCTTACGCATCT

GTGCGGTATTTCACACCGCATATATGGTGCACTCTCAGTACAATCTGCTC

TGATGCCGCATAGTTAAGCCAGTATACACTCCGCTATCGCTACGTGACTG

GGTCATGGCTGCGCCCCGACACCCGCCAACACCCGCTGACGCGCCCTGAC

GGGCTTGTCTGCTCCCGGCATCCGCTTACAGACAAGCTGTGACCGTCTCC

GGGAGCTGCATGTGTCAGAGGTTTTCACCGTCATCACCGAAACGCGCGAG

GCAGCTGCGGTAAAGCTCATCAGCGTGGTCGTGAAGCGATTCACAGATGT

CTGCCTGTTCATCCGCGTCCAGCTCGTTGAGTTTCTCCAGAAGCGTTAAT

GTCTGGCTTCTGATAAAGCGGGCCATGTTAAGGGCGGTTTTTTCCTGTTT

GGTCACTGATGCCTCCGTGTAAGGGGGATTTCTGTTCATGGGGGTAATGA

TACCGATGAAACGAGAGAGGATGCTCACGATACGGGTTACTGATGATGAA

CATGCCCGGTTACTGGAACGTTGTGAGGGTAAACAACTGGCGGTATGGAT

GCGGCGGGACCAGAGAAAAATCACTCAGGGTCAATGCCAGCGCTTCGTTA

ATACAGATGTAGGTGTTCCACAGGGTAGCCAGCAGCATCCTGCGATGCAG

ATCCGGAACATAATGGTGCAGGGCGCTGACTTCCGCGTTTCCAGACTTTA

CGAAACACGGAAACCGAAGACCATTCATGTTGTTGCTCAGGTCGCAGACG

TTTTGCAGCAGCAGTCGCTTCACGTTCGCTCGCGTATCGGTGATTCATTC

TGCTAACCAGTAAGGCAACCCCGCCAGCCTAGCCGGGTCCTCAACGACAG

GAGCACGATCATGCGCACCCGTGGGGCCGCCATGCCGGCGATAATGGCCT

GCTTCTCGCCGAAACGTTTGGTGGCGGGACCAGTGACGAAGGCTTGAGCG

AGGGCGTGCAAGATTCCGAATACCGCAAGCGACAGGCCGATCATCGTCGC

```
GCTCCAGCGAAAGCGGTCCTCGCCGAAAATGACCCAGAGCGCTGCCGGCA
CCTGTCCTACGAGTTGCATGATAAAGAAGACAGTCATAAGTGCGGCGACG
ATAGTCATGCCCCGCGCCCACCGGAAGGAGCTGACTGGGTTGAAGGCTCT
CAAGGGCATCGGTCGAGATCCCGGTGCCTAATGAGTGAGCTAACTTACAT
TAATTGCGTTGCGCTCACTGCCCGCTTTCCAGTCGGGAAACCTGTCGTGC
CAGCTGCATTAATGAATCGGCCAACGCGCGGGGAGAGGCGGTTTGCGTAT
TGGGCGCCAGGGTGGTTTTTCTTTTCACCAGTGAGACGGGCAACAGCTGA
TTGCCCTTCACCGCCTGGCCCTGAGAGAGTTGCAGCAAGCGGTCCACGCT
GGTTTGCCCCAGCAGGCGAAAATCCTGTTTGATGGTGGTTAACGGCGGGA
TATAACATGAGCTGTCTTCGGTATCGTCGTATCCCACTACCGAGATGTCC
GCACCAACGCGCAGCCCGGACTCGGTAATGGCGCGCATTGCGCCCAGCGC
CATCTGATCGTTGGCAACCAGCATCGCAGTGGGAACGATGCCCTCATTCA
GCATTTGCATGGTTTGTTGAAAACCGGACATGGCACTCCAGTCGCCTTCC
CGTTCCGCTATCGGCTGAATTTGATTGCGAGTGAGATATTTATGCCAGCC
AGCCAGACGCAGACGCGCCGAGACAGAACTTAATGGGCCCGCTAACAGCG
CGATTTGCTGGTGACCCAATGCGACCAGATGCTCCACGCCCAGTCGCGTA
CCGTCTTCATGGGAGAAAATAATACTGTTGATGGGTGTCTGGTCAGAGAC
ATCAAGAAATAACGCCGGAACATTAGTGCAGGCAGCTTCCACAGCAATGG
CATCCTGGTCATCCAGCGGATAGTTAATGATCAGCCCACTGACGCGTTGC
GCGAGAAGATTGTGCACCGCCGCTTTACAGGCTTCGACGCCGCTTCGTTC
TACCATCGACACCACCACGCTGGCACCCAGTTGATCGGCGCGAGATTTAA
TCGCCGCGACAATTTGCGACGGCGCGTGCAGGGCCAGACTGGAGGTGGCA
ACGCCAATCAGCAACGACTGTTTGCCCGCCAGTTGTTGTGCCACGCGGTT
GGGAATGTAATTCAGCTCCGCCATCGCCGCTTCCACTTTTTCCCGCGTTT
TCGCAGAAACGTGGCTGGCCTGGTTCACCACGCGGGAAACGGTCTGATAA
GAGACACCGGCATACTCTGCGACATCGTATAACGTTACTGGTTTCACATT
CACCACCCTGAATTGACTCTCTTCCGGGCGCTATCATGCCATACCGCGAA
AGGTTTTGCGCCATTCGATGGTGTCCGGGATCTCGACGCTCTCCCTTATG
CGACTCCTGCATTAGGAAGCAGCCCAGTAGTAGGTTGAGGCCGTTGAGCA
CCGCCGCCGCAAGGAATGGTGCATGCAAGGAGATGGCGCCCAACAGTCCC
CCGGCCACGGGCCTGCCACCATACCCACGCCGAAACAAGCGCTCATGAG
CCCGAAGTGGCGAGCCCGATCTTCCCCATCGGTGATGTCGGCGATATAGG
CGCCAGCAACCGCACCTGTGGCGCCGGTGATGCCGGCCACGATGCGTCCG
GCGTAGAGGATCGAGATCGATCTCGATCCCGCGAAATTAATACGACTCAC
TATAGGGGAATTGTGAGCGGATAACAATTCCCCAAATAATTTTGTTTAAC
TTTAAGAAGGAGATATACATATGCAGATCTTCGTGAAGACTTTGACCGGT
AAAACCATAACATrGGAAGTTGAATCTTCCGATACCATCGACAACGTTAA
GTCGAAAATTCAAGACAAGGAAGGTATCCCTCCAGATCAACAAAGATTGA
TCTTTGCCGGTAAGCAGCTAGAAGACGGTAGAACGCTGTCTGATTACAAC
ATTCAGAAGGAGTCCACCTTACATCTGGTGCTAAGGCTCCGCGGggggtc
caaactcctgccgcgattgccgggagtcccctcttcttcatgtcaacgtg
ggtacaagggagtctggcggggcgacggcatcatgcaaaccacctgccca
tgtggagcacagatcaccggacatgtgaaaaacggttccatgaggatcgt
ggggcctaggacctgtagtaacacgtggcatggaacattccccattaacg
cgtacaccacgggccctgcacgccctccccggcgccaaattattctagg
gcgctgtggcgggtggctgctgaggagtacgtggaggttacgcgggtggg
ggatttccactacgtgacgggcatgaccactgacaacgtaaagtgcccgt
gtcaggttccggccccgaattcttcacagaagtggatggggtgcggttg
cacaggtacgctccagcgtgcaaaccctcctacgggaggaggtcacatt
cctggtcgggctcaatcaatacctggttgggtcacagctcccatgcgagc
ccgaaccggacgtagcagtgctcacttccatgctcaccgaccccctccac
attacggcggagacggctaagcgtaggGGTACCGACGACGACGACAAGGC
CATGGCGATATCGGATCCGAATTCGAGCTCCGTCGACAAGCTTGCGGCCG
CACTCGAGCACCACCACCACCACCACTGAGATCCGGCTGCTAACAAAGCC
CGAAAGGAAGCTGAGTTGGCTGCTGCCACCGCTGAGCAATAACTAGCATA
ACCCCTTGGGGCCTCTAAACGGGTCTTGAGGGGTTTTTTGCTGAAAGGAG
GAACTATATCCGGAT.
```

The HCV NS5A insert sequence is shown in lowercase font.

Cells were grown at 37° C. and 250 r.p.m until an $OD_{600}$ of 0.55 was reached. Cells were then chilled at 4° C. for 30 minutes, induced with 1 mM IPTG, and incubated for 5 hours at 25° C. and 250 r.p.m. Cells were then collected by centrifugation at 6,000×g for 10 minutes and resuspended in 20 ml of buffer C (25 mM Tris-HCl (pH8.0), 25 mM NaCl) per liter. Cells were lysed by three passes through a cold Avestin air emulsifier at 15,000 p.s.i. Following lysis, cell extracts were clarified at 25,000×g for 30 minutes at 4° C. Clarified extracts were fractionated by ammonium sulfate precipitation, with the bulk of NS5A-Domain I-Δh present in the 5-25% saturation pellet. Ammonium sulfate pellets were resuspended in 10 ml of buffer C and applied to a HiPrep 26/10 desalting column at a flow rate of 8 ml/min (Amersham/Pharmacia). The desalted protein was then loaded onto a HiPrep 16/20 DEAE column equilibrated with buffer C at 2.5 ml/min and eluted with a linear 500 mM NaCl gradient. Pooled DEAE elution fractions were then loaded on a 5 ml bed volume HiTrap IMAC column (Amersham/Pharmacia) equilibrated with buffer C at a flow rate of 2.5 ml/minunte. Following extensive washing with buffer C and buffer C supplemented with 1 M NaCl, NS5A-Domain I-Δh was eluted with a 25 ml linear gradient of buffer C supplemented with 250 mM imidazole. Fractions containing NS5A-Domain I-Δh were pooled and exchanged into buffer A (25 mM Tris-HCl (pH 8.0), 25 mM NaCl, 20% glycerol) using a HiPrep 26/10 desalting column at a flow rate of 8 ml/min (Amersham/Pharmacia). Following this initial purification, the C-terminal polyhistidine tag and linker sequence were proteolytically removed from NS5A-Domain I-Δh by on overnight incubation at 25° C. in the presence of recombinant light chain enterokinase protease.

The cleaved protein product had the following amino acid sequence:

(SEQ ID NO: 4)
SKLLPRLPGVPFFSCQRGYKGVWRGDGIMQTTCPCGAQITGHVKNGSMRI

VGPRTCSNTWHGTFPINAYTTGPCTPSPAPNYSRALWRVAAEEYVEVTRV

GDFHYVTGMTTDNVKCPCQVPAPEFFTEVDGVRLHRYAPACKPLLREEVT

FLVGLNQYLVGSQLPCEPEPDVAVLTSMLTDPSHITAETAKRGTDDDDK.

Once cleavage was complete, the protein was re-purified by ion exchange on a HiPrep 16/20 DEAE column using conditions described previously. This step removed the protease and tag from Domain I-Δh protein. The protein was then exchanged into buffer A (25 mM Tris-HCl pH 8.0, 175 mM NaCl, and 20% (v/v) glycerol) using a HiPrep 26/10 desalting column (Amersham/Pharmacia). Protein was then concentrated to 20-30 mg/ml via Amicon ultra 4 centrifugal concentrators. Protein yields were typically between 10 and 12 mg/L of bacterial culture at an estimated 95% purity. The modification of Domain I by the removal of the amino-terminal membrane anchor has allowed for the production of large quantities of soluble protein that can be purified in the absence of detergents, providing an ideal material for structural and biochemical analyses. Additionally, the use of a long carboxy-terminal linker between the end of the domain I coding sequence and the polyhistidine fusion tag greatly increased the solubility of domain I as well as increasing the fraction of protein bound to columns in IMAC chromatography.

Crystal Growth and Freezing

Crystals of NS5A Domain I-Δh were grown by hanging drop vapor diffusion at 4° C. on siliconized cover slips in 24 well Linbro plates. The 1 milliliter of well solution contained 100 mM HEPES pH 7.0, 0.6 M trisodium citrate dihydrate, and 13% (v/v) isopropanol. The drop contained 1.5 microliters of Domain I-Δh protein at 26 mg/ml in buffer A, 1.25 microliters of well solution, and 0.5 microliters of 2 M non-detergent sulfobetaine 201. Crystals of 0.15-0.3 mm in size grew from these conditions in approximately 8 days. For freezing, crystals were transferred from hanging drops to a 2 microliter drop of well solution plus 20% (v/v) glycerol and incubated at 4° C. for ten minutes. Crystals were then transferred to a 2 microliter drop of well solution with a total of 30% (v/v) glycerol and allowed to equilibrate for 10 minutes. Crystals were then harvested and flash frozen in liquid propane.

Data Collection

All data collection was performed at beam line X9A at Brookhaven National Labs National Synchrotron Light Source. As no selenomethionine labeled protein could be obtained, phases were determined from the endogenous zinc present in NS5A. Prior to diffraction data collection, XAFFS scans were used to confirm the presence of zinc in the protein crystals and determine the zinc K absorption edge. For zinc multiwavelength anomalous diffraction (MAD), data were collected at the zinc absorption maxima (9660 eV, 1.28345 Å), the maxima inflection point (9657 eV, 1.28385 Å), and at a remote wavelength (9757 eV, 1.27069 Å). All three data sets were collected as 1° oscillations at a detector distance of 140 mm with 30 second image exposures at 100 Kelvin. For each data set, a total of 120° degrees of data was collected. Data collection was limited to 2.5 Å resolution by a combination of detector geometry and the presence of an unusually long axis in the crystal.

Data Processing and Model Building

Data were processed and scaled from 30-2.5 Å resolution using DENZO/SCALEPACK (Otwinowski, Z. & Minor, M. in *Macromolecular Crystallography, part A*, 307-326 (Academic Press (New York), 1997)). Data was scaled to a $P4_122$ spacegroup. The unit cell dimensions were determined to be a,b=55.28 Å, c=312.30 Å, α,β,γ=90', with two NS5A molecules per asymmetric unit. The scaled, processed data for each of the three MAD wavelength datasets was then used to locate anomalous peaks corresponding to the presence of the zinc atom in NS5A Domain I. The 2 zinc sites were found by the program SOLVE (Terwilliger, T. C. & Berendzen, J. Automated MAD and MIR structure solution. *Acta Crystallogr D Biol Crystallogr* 55 (Pt 4), 849-61 (1999)). An interpretable electron density map was obtained using MLPHARE followed by density modification and phase combination by DM (Collaborative Computational Project, N. The CCP4 suite: programs for protein crystallography. *Acta Crystallogr D Biol Crystallogr* 50, 760-3 (1994)). The remote (9757 eV, 1.27069 Å) data set was used for electron density map calculation, as this data set was collected immediately following a synchrotron storage ring fill, and therefore was collected with a more intense x-ray beam than the other MAD data sets. Several rounds of iterative model building and refinement were performed using the programs O (Jones, T. A., Zou, J. Y., Cowan, S. W. & Kjeldgaard. Improved methods for building protein models in electron density maps and the location of errors in these models. *Acta Crystallogr A* 47 (Pt 2), 110-9 (1991)) and CNS (Brunger, A. T. et al. Crystallography & NMR system: A new software suite for macromolecular structure determination. *Acta Crystallogr D Biol Crystallogr* 54 (Pt 5), 905-21 (1998)). The final model contained 96 solvent molecules, two zinc atoms, and two molecules of NS5A consisting of amino acids 36-198 of NS5A, with density not observed for the extreme amino and C-termini. A summary of the final refinement statistics is provided in table 1. The final model has an R-factor of 22.1% and free R-factor of 28.6%, with r.m.s.d. on bond lengths and angles of 0.00625 Å and 1.34°, respectively. The thermal parameter r.m.s.d. values are 1.28 $Å^2$ for mainchain atoms and 2.15 $Å^2$ for sidechain atoms. PROCHECK (Laskowski, R. A., et al. *J Mol Biol* 231, 1049-67 (1993)) revealed no unfavorable (φ,ψ) combinations, and mainchain and side chain structural parameters consistently better than or within the average for structures refined to 2.5 Å. Atomic coordinates have deposited in the Protein Data Bank. Secondary structures were assigned using the program DSSP (Kabsch W., a. S., C. *Biopolymers* 22, 2577-2637 (1983)). Graphics presented in this manuscript were generated using the programs PyMOL (DeLano, W. L. (world wide web at pymol.org, 2002)). APBS was used for calculating surface potentials (Baker, N. A., et al. *Proc Natl Acad Sci USA* 98, 10037-41 (2001)). Sequence alignments were performed using ClustalX (Thompson, J. D., et al. *Nucleic Acids Res.* 24, 4876-4882 (1997)) and plotting of conservation to molecular surfaces was performed using the program msf_similarity_to_pdb (Dr. David Jeruzalmi, personal communication).

Example 1

Architecture of NS5A Domain I

The crystal structure of domain I revealed two essentially identical monomers per asymmetric unit packed together as a dimer via contacts near the N-terminal ends of the molecules. A summary of the data collection and processing statistics is provided in table 1.

TABLE 1

Summary of data collection and refinement statistics

Data Collection

| Wavelength (Å) | Resolution (Å) | Reflections measured/unique | Completeness[a] (%) | $R_{sym}^{a,b}$ (%) | $I/\sigma(I)^a$ | Phasing Power[c] (anomalous) |
|---|---|---|---|---|---|---|
| λ1 = 1.28345 | 30.0-2.50 | 301,420/17,992 | 100 (99.9) | 6.9 (32) | 23.8 (4.7) | 1.18 |
| λ2 = 1.28385 | 30.0-2.50 | 302,219/17,992 | 100 (99.9) | 4.5 (34) | 22.4 (4.3) | 1.25 |
| λ3 = 127069 | 30.0-2.50 | 314,341/18,007 | 100 (100) | 8.7 (27) | 35.6 (5.7) | 1.21 |
| figure of merit | acentric 0.48 | centric 0.40 | overall 0.46 | | | |

Refinement against λ3

| Resolution (Å) | Cut-off | Reflections | Completeness (%) | $R_{cryst}^d$ (%) | $R_{free}^e$ (%) |
|---|---|---|---|---|---|
| 30.0-2.50 | $|F|/\sigma|F| > 2.0$ | 29,570 | 92.5 | 22.1 | 28.6 |

Root mean square deviations

| Bond lengths | Bond angles | Thermal parameters mainchain atoms | Thermal parameters sidechain atoms |
|---|---|---|---|
| 0.00625 Å | 1.34° | 1.28 Å$^2$ | 2.15 Å$^2$ |

[a]Values reported in the format: overall data (last resolution shell)
[b]$R_{sym} = \Sigma|I - <I>|/\Sigma I$, where I is observed intensity and <I> is average intensity obtained from multiple observations of symmetry-related reflections.
[c]Phasing power = rms ($|F_H|/E$), where $|F_H|$ = heavy atom structure factor amplitude and E = residual lack of closure.
[d]$R_{cryst} = \Sigma|F_{obs} - F_{calc}|/\Sigma|F_{obs}|$, where $F_{obs}$ and $F_{calc}$ are the observed and calculated structure factors, respectively.
[e]$R_{free}$ is the same as $R_{cryst}$, but is calculated with 10% of the data.

Figure 1D:
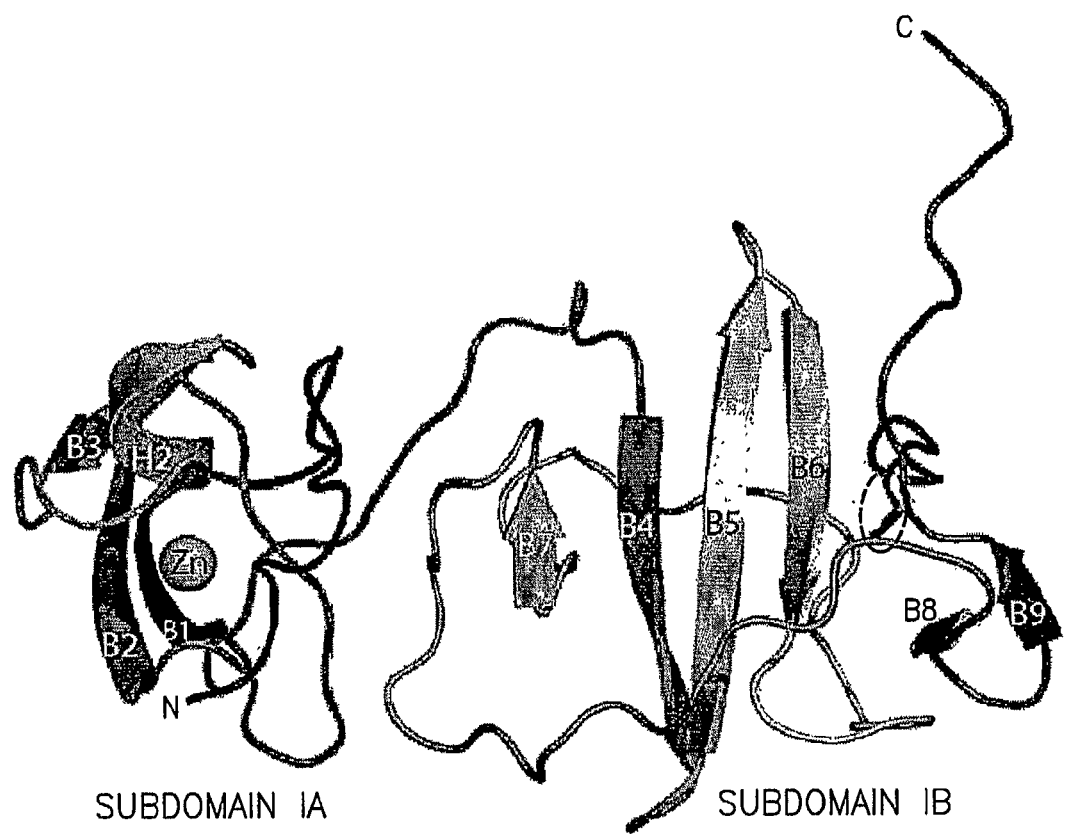
Figure 1E:
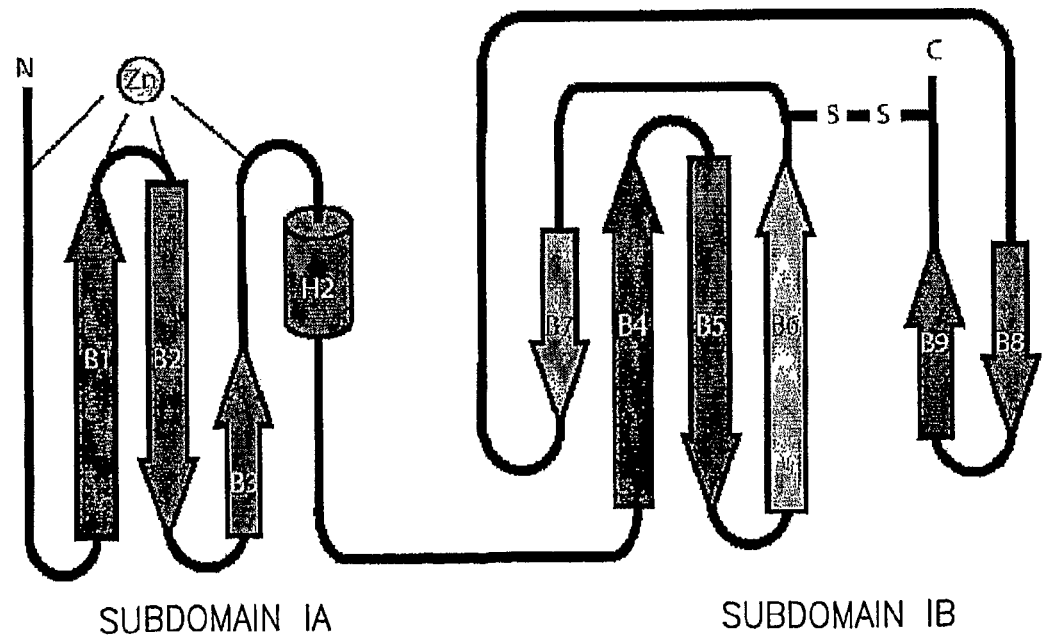

Domain I consists of 9 β-strands (referred to as B1-B9) and a single short α-helix connected by an extensive network of extended loop regions. This helix has been designated H2 to allow numbering of the previously determined N-terminal membrane anchoring helix H1. These loop regions comprise a surprising 62% of the domain I structure, with a number of large (14 or more amino acids) extended random coil elements. For ease of discussion, the molecule is divided into two subdomains; the N-terminal subdomain IA containing β-strands B1, B2 and B3, and the α-helix H2 (FIGS. 1b-e), and the C-terminal subdomain IB containing the remaining 6 β-strands (best seen in FIG. 1d). The large extended loop regions make tracing the C-α backbone difficult in conventional ribbon models, so a more schematic view of the fold of domain I is shown in FIG. 1e. The structure of subdomain IA consists of an N-terminal extended loop lying adjacent to a 3-stranded anti-parallel β-sheet, with H2 at the C-terminus of the third β-strand. The elements comprise the structural scaffold for a four-cysteine zinc atom coordination site at one end of the β-sheet. A long stretch of random coil exits H2 and passes across the β-sheet and N-terminal strand in an orientation orthogonal to the plane of the sheet. This coiled sequence then enters a tight turn and runs adjacent to the β-sheet away from the zinc atom, towards what is referred to as the 'bottom' of subdomain IA, before entering a proline rich region that connects subdomain IA to subdomain IB. Domain IB consists of a four-strand anti-parallel β-sheet (B4, B5, B6, and B7) and a small two-strand anti-parallel β-sheet near the C-terminus (B8 and B9) surrounded by extensive random coil structures. A disulfide bond in subdomain IB connects the B6/B7 loop and the C-terminal loop region. The search for proteins with similar fold architecture to domain I using the DALI server was unsuccessful at identifying related structures, indicating domain I represents a unique protein fold.

Example 2

The NS5A Zinc Binding Site

Figure 2B:
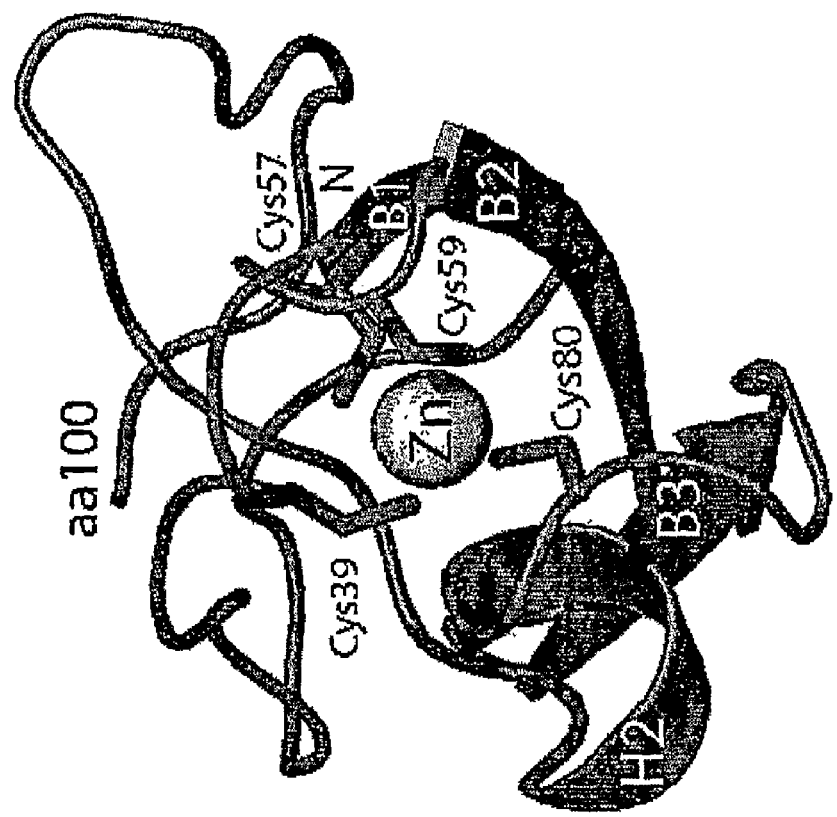
FIG. 2 schematically depicts the NS5A zinc-binding motif and disulfide bond. A. A view of the subdomain 1A region of NS5A (amino acids 36-100) highlighting the zinc-binding motif. The zinc atom is coordinated by four cysteine residues indicated in the figure. B. A 'top down' view of the zinc ion coordination site showing caging of the zinc atom. Residues and secondary structure elements are labeled as in FIG. 1a. C. Domain I monomer with the disulfide bond in subdomain Ib circled. The positions of cysteines 142 and 190 are also indicated. The disulfide bond connects an extended loop region C-terminal to B6 to the extreme C-terminus of domain I. D. Overlay of initial experimental electron density map on the model of the disulfide bond at 1σ. Amino acids cysteine 142 and 190 are labeled.
Figure 2A:
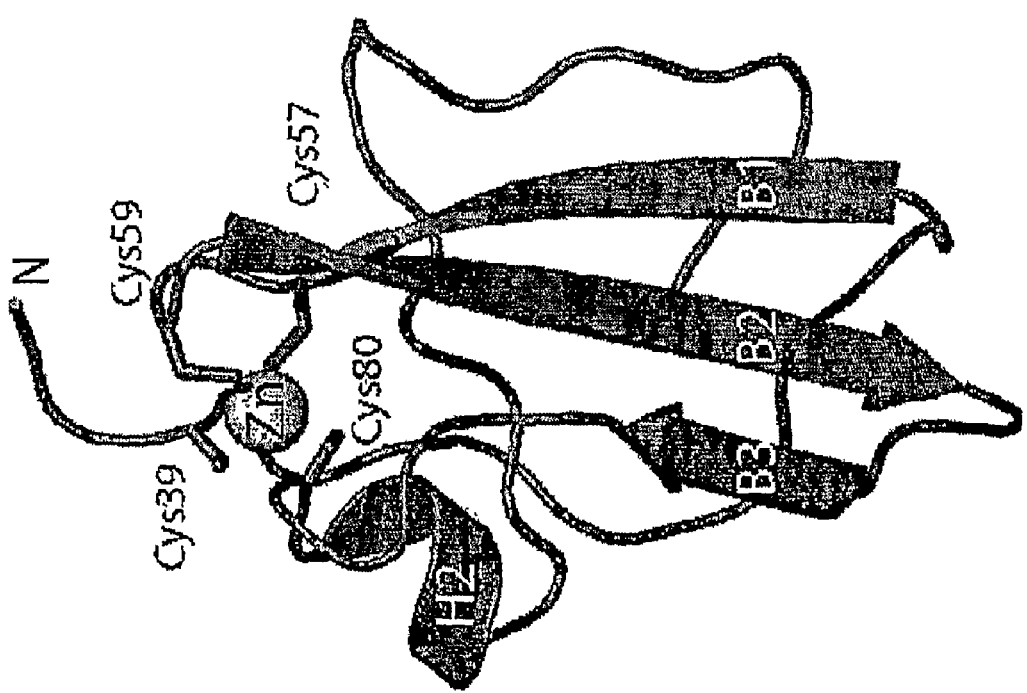

Previous experiments have demonstrated the coordination of a single zinc atom by the domain I region of NS5A. The coordination of this metal ion is absolutely required for RNA replication. The location of the four cysteines involved in zinc coordination (Cys 39, Cys 57, Cys 59, and Cys 80), in relation to predicted secondary structures surrounding these residues, suggested a model of the zinc binding site, that of a four stranded anti-parallel β-sheet with the zinc atom coordinated at one end of the sheet. Overall, the proposed model is quite similar to the actual organization of the NS5A zinc-binding site revealed herein. A view of subdomain IA (aa 36-100) highlighting the cysteine residues involved in zinc ion coordination is shown in FIGS. 2a and 2b. The anti-parallel β-sheet, composed of strands B1, B2, and B3, positioning Cys 57, Cys 59, and Cys 80 near the zinc-binding site is essentially as predicted. The long random coil region positioning Cys 39 and connecting the N-terminus to the β-sheet was incorrectly predicted to be a long β-strand, but the arrangement of this region in relation to the other strands matches the original model. *Helix* H2 and the loop regions following H2 are not part of the original predicted site, but likely play an important role in this fold. The four cysteine ligands all lie within loop regions. Cys 39 is within the large N-terminal loop, Cys 57 and Cys 59 are positioned in the loop between strands B1 and B2, and Cys 80 is positioned in the long loop connecting B3 to H2. The distances of the cysteine side chain sulfur groups to the zinc atom for Cys 39 (2.36 Å), Cys 57 (2.47 Å), Cys 59 (2.42 Å) and Cys 80 (2.45 Å) observed in domain I are close to the ideal 2.35 (+/−0.09) Å distances for structural metal zinc coordination sites in proteins. Similarly, the side chain geometries are within the acceptable limits of previously published values.

DALI database searches of the subdomain IA region were unable to locate similar metal binding folds. A survey of zinc containing proteins with known structures was also unsuccessful at identifying proteins that coordinate metal ions like NS5A. The location of the zinc-binding site in the structure of domain I, combined with previous biochemical characterization, strongly suggests this ion plays a structural role in NS5A fold maintenance. The presence of a novel metal ion coordination motif, combined with the previous demonstration that zinc binding is essential for replication, provides an interesting potential anti-viral drug design target.

Example 3

NS5A Domain I has a C-Terminal Disulfide Bond

Figure 2C:
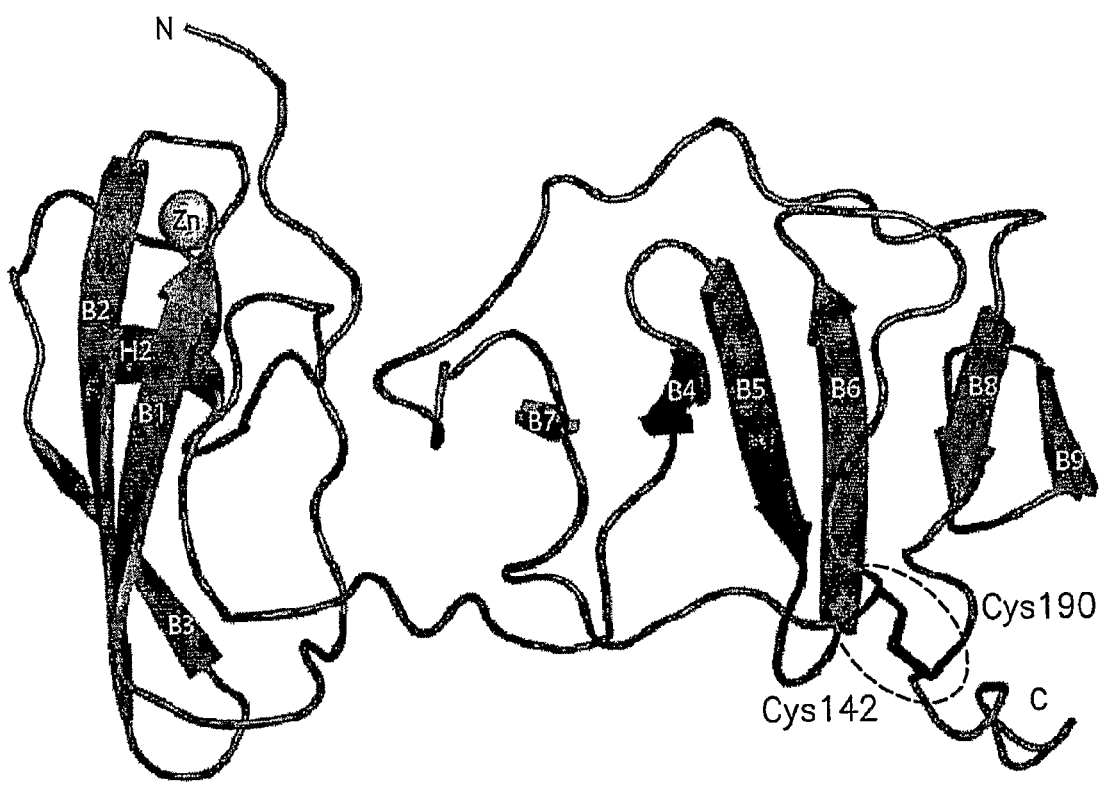
Figure 2D:
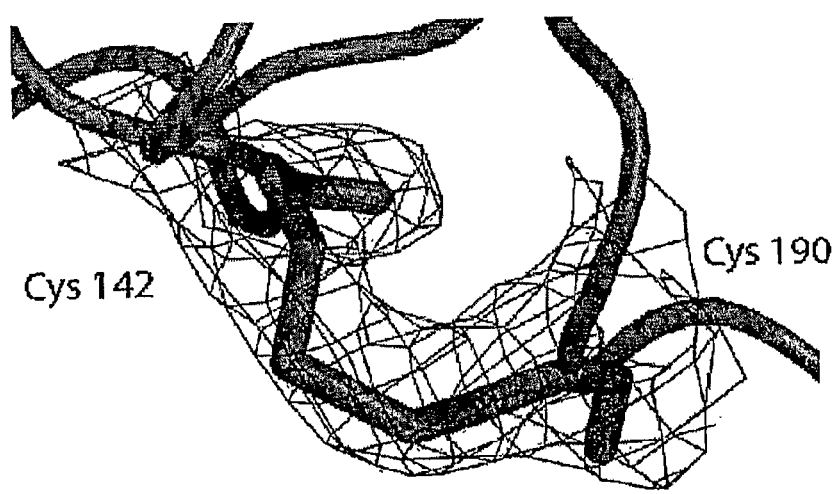

Perhaps the most surprising observation from model building and refinement of the structure was the presence of a disulfide bond near the C-terminus of domain I. The disulfide bond connects the sidechains of the conserved Cys 142 and Cys 190, resulting in a covalent link between the loop exiting from β-strand B6 to the C-terminal extension of strand B9 (FIG. 2c). Model refinement without a disulfide at this position placed the sidechains of these cysteine residues in an unfavourable proximity. Refinement with the disulfide led to no problematic geometry for either cysteine residues, and generated a model that better fit the electron density (FIG. 2d). Density corresponding to the disulfide bond is present in both molecules of domain I in the asymmetric unit, providing two independent views of this feature. The disulfide bond in the model results in a sulfur-to-sulfur atom distance of 2.03 Å, an ideal value for bond formation. Although all evidence points to the presence of a disulfide bond in the protein crystal, it is not yet clear if this bond exists in NS5A in the context of an HCV infection. Experiments are currently underway to determine if this disulfide exists in purified NS5A, and more importantly, in NS5A extracted from cells bearing replicating HCV RNAs.

It has long been held that disulfide bonds only occur in cytoplasmic proteins that are involved in oxidative/reductive chemistry. However, recent publications have shown that the cytoplasm is not as reducing as originally thought, and that transient disulfide bonds can be formed. It is important to consider that NS5A is primarily present, not in the cytoplasm at large, but in a replicase complex, a structure involving considerable ER membrane alterations that represents a unique cytoplasmic microenvironment in which an oxidizing environment could exist. Recently, a number of thiol containing cytoplasmic proteins have been shown to use reactive oxygen species (ROS) to rapidly regulate protein conformation and activity via reversible disulfide bond formation. These proteins use ROS as a switch to regulate their activities by metal ion release and subsequent disulfide bond formation under conditions of oxidative stress. NS5A has been shown to induce oxidative stress and ROS in the context of replicating viral RNA in cell culture, leading to an inhibition of the anti-apoptotic properties of NF-κB. However, the role of ROS in HCV biology is controversial, as ROS have been shown to both stimulate and inhibit HCV RNA replication in cell culture. It is not yet clear what role, if any, is played by ROS and NS5A in HCV biology, but the presence of a potential regulatory disulfide bond in NS5A makes this an interesting and testable hypothesis. Independent of ROS, a number of cytoplasmic proteins, including those of viruses, have been shown to contain transient disulfide bonds, often serving regulatory activities for these proteins. Perhaps this is the case for NS5A.

Mutagenesis of the Cys 142 and Cys 190 residues produced no measurable defect in HCV RNA replication, indicating the disulfide bond is not required for the replicase functions of NS5A. However, it is enticing to imagine the disulfide bond, tethering the C-terminus of domain I and likely altering the arrangement of the C-terminal domain II and III, plays a regulatory role in NS5A function, serving as a conformation switch to modulate functions of NS5A in and out of the replicase.

Example 4

Analysis of the Molecular Surfaces of Domain I

FIG. 3a presents three rotational views of the solvent accessible surface of domain I colored by electrostatic potential. The orientations, left to right, are identical to those shown in ribbon diagrams in FIGS. 1b,c, and d, respectively. Overall these views highlight the strikingly uneven charge distribution within domain I. The N-terminal subdomain IA region has an almost exclusively basic surface, whereas the C-terminal subdomain IB is predominantly acidic. This unusual charge distribution has interesting implications in the dimeric form of the protein (see below).

Analysis of the conservation of residues comprising the surface of domain I was performed to define conserved surfaces that might represent sites of interaction or active sites for domain I. A conservation plot, based on sequence alignments of NS5A domain I regions from the 30 HCV genotype reference sequences from the Los Alamos HCV sequence database as well as the sequence of the related GB virus B NS5A, has been generated (FIG. 3b). The plot shows the significant overall surface conservation of domain I, and highlights a large patch of conserved residues that may represent a molecular interaction surface. The major components of this surface are isoleucine 90, tryptophan 111, proline 141, gulatmine 143, proline 145, histidine 159, glycine 178, proline 192, and glutamate 193. This contiguous conserved surface spans subdomain IA and IB, including a prominent 'pocket' generated by the interface between these elements. An electrostatic potential plot of this same surface is also shown, highlighting the complex mixture of acidic, basic, and hydrophobic residues generating this surface (FIG. 3c). A ribbon diagram of this orientation of domain I is shown in FIG. 3d. A large number of proteins have been shown to interact with the domain I region of NS5A, any or all of which may interact with this surface.

Example 5

A Dimeric NS5a Reveals Potential Molecular Interaction Surface

Figure 4A:
FIG. 4 shows that the NS5A domain I dimer potential interaction surfaces. A. Ribbon diagrams of four rotations of the domain I dimer. The relative rotation of each image is indicated. B. Surface potential plots of the domain I dimer, views correspond to those shown as ribbon diagrams in A. Analysis of images in A and B reveal the dimer creates a relatively flat, basic surface near the N-terminus of NS5A and a large groove between the two domain IB regions. This very basic groove is flanked by more acidic 'arm' regions. C. Model of NS5A position relative to the ER membrane. The basic amino terminal surface is likely close to the cytoplasmic face of the ER, based on the proximity of this region to the putative membrane anchor. The basic charge of this surface is likely involved in charge neutralization of acidic lipid head groups. This orientation positions the large basic groove of NS5A away from the membrane where it can interact with RNA.
Figure 4A:
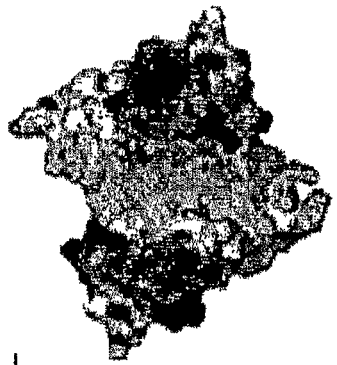

Another surface of domain I that was of considerable interest was the buried region between monomers to create the dimeric domain I seen in the crystal structure. These contact surfaces have been colored in white on a green solvent accessible surface diagram of a domain I monomer in FIG. 3e. FIG. 3f presents a surface conservation plot highlighting these interaction patches (view orientation is identical to FIG. 1d). The dimer interface of 678 Å$^2$ consists of two patches of buried surface area, one located primarily in subdomain IA, and a second located in subdomain IB. The total buried surface area in the domain I dimer is more than the generally accepted standard of 600 Å$^2$ for protein interfaces and has good shape and electrostatic complementarity. The contact patch in subdomain IA contains a number of conserved residues, whereas the smaller patch in subdomain IB is of lower sequence conservation. It is important to note that residues of lower conservation involved in the dimer interface appear to primarily be involved in main chain contacts, suggesting some sequence plasticity is allowable at these positions. The zinc-binding site is close to the interface between monomers and may represent a factor involved in NS5A oligomerization. Homotypic oligomeric interactions of the NS5A protein in yeast two-hybrid and pull down experiments have recently been described. Preliminary analytical ultracentrifugation experiments suggest domain I is monomeric in solution, although it is important to note that these experiments were performed with only a portion of NS5A protein in the absence of membranes or nucleic acids. Perhaps the conditions that favor protein-protein interactions in crystallization have captured a glimpse of part of the relevant NS5A oligomerization interactions. Clearly more work is needed to determine the oligomeric state of the NS5A protein. Nonetheless, the dimeric form of domain I observed in the crystal structure provides a number of interesting features that may have relevance to HCV biology. FIG. 4a presents three rotations of the dimer showing the interface between monomers and the large groove between the domain IB regions of chain A and B generated by the "claw-like" shape of the dimer.

Figure 4B:
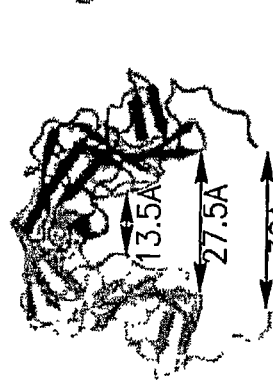
Figure 4B:

As NS5A likely makes contacts with proteins, RNA, and membranes, an analysis of the protein electrostatic surface potential is especially important in determining how a dimeric domain I might fit into the replicase (FIG. 4b). One interesting feature in these surface potential plots is the very basic surface of domain I where the N-termini of the dimer are located. An NMR structure of the first 31 amino acids of NS5A has recently shown amino acids 5-25 form the H1 amphipathic helix membrane anchor. The NMR helix structure and the present domain I crystal structure are separated by only five amino acids, suggesting the N-terminus of domain I is likely close to the membrane. The presence of a basic surface on the portion of domain I close to the N-terminus is logical, as the protein is likely to be in close contact with the negatively charged lipid head groups of the membrane. This interaction would position the groove generated by the domain I dimer to face away from the membrane where it could interact with RNA. This large groove is an attractive nucleic acid binding pocket, especially when surface potentials of the highly basic groove are plotted. Modeling studies suggest this groove is of sufficient dimensions to bind to either single or double stranded RNA molecules. The deep, highly basic portion of the groove has a diameter of 13.5 Å. The more hydrophobic boundary of the basic groove is considerably larger, with a diameter of 27.5 Å. A dsRNA molecule with a diameter of approximately 20 Å, could easily fit in the groove, making both electrostatic contacts with the deep basic groove and hydrophobic contacts with the groove boundary region. The electrostatic character of the groove is conserved among HCV sequences, suggesting this may be an important functional feature. Interactions of NS5A with nucleic acids during protein purification have been described, although specific RNA binding of NS5A remains to be demonstrated. The 'arms' extending out past this groove are more acidic, perhaps serving as a clamp to prevent RNA from exiting the groove. The inside of the acidic arms lining the groove are separated by about 32 Å. The positioning of NS5A domain II and III relative to the groove remains unclear, but it is interesting to imagine these domains interact with the RNA positioned by the domain I groove. Furthermore, the dimeric form of domain I places the conserved interaction surface described for the monomer on the outside of the 'arms' of the dimer, where they would be available for other interactions.

Figure 4C:
Figure 4C:
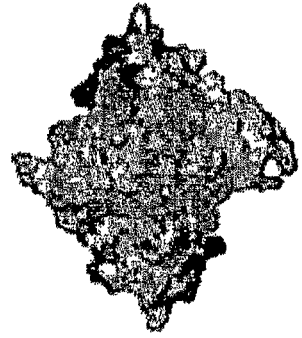
Figure 4C:
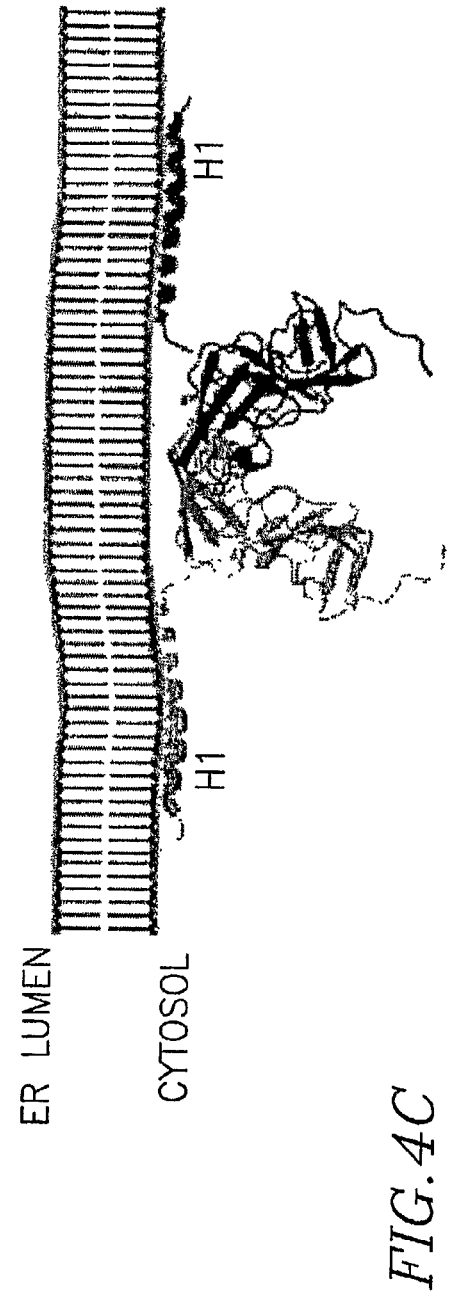

A model of the NS5A dimer in relation to the cellular membrane and membrane anchor is presented in FIG. 4c, which provides a preliminary means of identifying possible RNA and protein interaction surfaces, through the positioning of the dimeric domain I relative to the membrane surface, which will ultimately provide a wealth of information regarding the interactions of NS5A within the replicase.

The presence of the disulfide bond in purified preparations of domain I NS5A protein used in the crystallization experiments was investigated. Analysis of the electrophoretic mobility of domain I NS5A under reducing and non-reducing conditions on sodium dodecyl sulfate polyacrylamide gels indicated the disulfide bond was present in the purified protein preparation and was not an artifact of protein crystallization (FIG. 5).

Example 6

NS5A Preferentially Binds Single Stranded RNA Molecules

Figure 6:
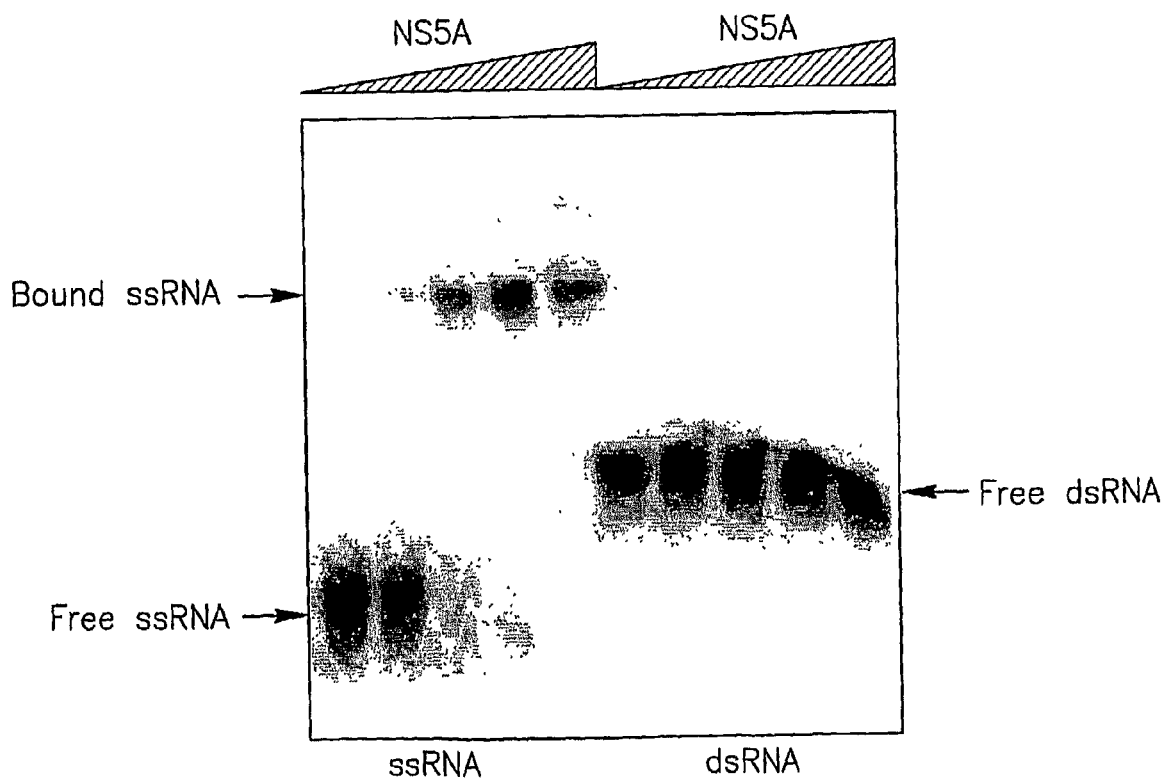
FIG. 6 shows the interaction of NS5A with RNA in an electrophoretic mobility shift assay. In this figure NS5A was allowed to interact with either single stranded RNA (ssRNA, left hand lanes) or double stranded RNA (dsRNA, right hand lanes) under conditions of increasing concentrations of NS5A (indicated by triangles on the top of the gel image). RNAs used were non-specific sequences generated by in vitro transcription of an irrelevant plasmid polylinker. The electrophoretic mobility of bands corresponding to free single and double stranded RNAs and RNAs bound to NS5A are indicated by arrows. NS5A appears to bind only single stranded RNAs in this assay, as evidence by the presence of a shifted complex (bound ssRNA) in the presence of NS5A. No binding of NS5A to double stranded RNA was observed in this assay.

The interaction of HCV NS5A with non-specific single and double stranded RNA molecules was also demonstrated in an in vitro binding assay based on electrophoretic mobility shift assay methods (FIG. 6). NS5A preferentially bound single stranded RNA molecules with very high affinities for target RNAs (approximately 10 nM dissociation constant). NS5A appeared to not interact with non-specific double stranded RNAs in this assay. The observed interaction in vitro and the structure of the domain I groove indicate RNA binding may be an important function of NS5A.

What is claimed is:

1. A method of identifying a Hepatitis C virus (HCV) inhibitor in an inhibitor screening assay comprising:

(a) determining the three-dimensional structure of the N-terminal domain I-Δh of an NS5A protein crystal, wherein said NS5A N-terminal domain I-Δh protein comprises a protein with at least 90% identity to amino acids 36-199 of SEQ ID NO: 4 and wherein said crystal has space group P4$_1$22 with unit cell dimensions of a=b=55.28Å, c=312.30 Å and α,β,γ=90°, (b) selecting or designing a potential inhibitor by performing rational drug design with said three-dimensional structure determined in part (a) wherein said selecting or designing is performed in conjunction with computer modeling;

(c) contacting said potential inhibitor with an N-terminal domain of an NS5A protein of hepatitis C virus; and (d) detecting an ability of said potential inhibitor for inhibiting infection or replication of a hepatitis C virus.

2. The method of claim 1, wherein said inhibitor interferes with zinc binding to said N-terminal domain of an NS5A protein.

3. The method of claim 1, wherein said inhibitor interferes with disulfide bridge formation between cysteine residues at positions 142 and 190 of said N-terminal domain of an NS5A protein.

4. The method of claim 1, wherein said inhibitor interferes with dimerization of NS5A proteins of said virus.

5. The method of claim 1, wherein said inhibitor interferes with the formation of a groove between two subdomain IB regions of N-terminal domains of dimerized NS5A.

6. The method of claim 1, wherein said inhibitor is positioned within a groove formed between two subdomain IB regions of N-terminal domains of dimerized NS5A.

7. The method of claim 1, wherein said inhibitor interacts with a binding site for zinc comprising a cysteine residue at positions 39, 57, 59, 80 or combinations thereof.

8. The method of claim 1, wherein said ability for inhibiting infection or replication of a hepatitis C virus is assayed in vivo or in vitro.

* * * * *

SEQUENCE LISTING

```
<160> NUMBER OF SEQ ID NOS: 4

<210> SEQ ID NO 1
<211> LENGTH: 301
<212> TYPE: PRT
<213> ORGANISM: Artificial
<220> FEATURE:
<223> OTHER INFORMATION: HCV NS5A domain I protein with an N-terminal
      ubiquitin fusion tag and a C-terminal fusion tag

<400> SEQUENCE: 1
```

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
                35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ser Lys Leu Leu
65                  70                  75                  80

Pro Arg Leu Pro Gly Val Pro Phe Phe Ser Cys Gln Arg Gly Tyr Lys
                85                  90                  95

Gly Val Trp Arg Gly Asp Gly Ile Met Gln Thr Thr Cys Pro Cys Gly
                100                 105                 110

Ala Gln Ile Thr Gly His Val Lys Asn Gly Ser Met Arg Ile Val Gly
            115                 120                 125

Pro Arg Thr Cys Ser Asn Thr Trp His Gly Thr Phe Pro Ile Asn Ala
        130                 135                 140

Tyr Thr Thr Gly Pro Cys Thr Pro Ser Pro Ala Pro Asn Tyr Ser Arg
145                 150                 155                 160

Ala Leu Trp Arg Val Ala Ala Glu Glu Tyr Val Glu Val Thr Arg Val
                165                 170                 175

Gly Asp Phe His Tyr Val Thr Gly Met Thr Thr Asp Asn Val Lys Cys
                180                 185                 190

Pro Cys Gln Val Pro Ala Pro Glu Phe Phe Thr Glu Val Asp Gly Val
            195                 200                 205

Arg Leu His Arg Tyr Ala Pro Ala Cys Lys Pro Leu Leu Arg Glu Glu
    210                 215                 220

Val Thr Phe Leu Val Gly Leu Asn Gln Tyr Leu Val Gly Ser Gln Leu
225                 230                 235                 240

Pro Cys Glu Pro Glu Pro Asp Val Ala Val Leu Thr Ser Met Leu Thr
                245                 250                 255

Asp Pro Ser His Ile Thr Ala Glu Thr Ala Lys Arg Gly Thr Asp Asp
            260                 265                 270

Asp Asp Lys Ala Met Ala Ile Ser Asp Pro Asn Ser Ser Ser Val Asp
        275                 280                 285

Lys Leu Ala Ala Ala Leu Glu His His His His His
                290                 295                 300

<210> SEQ ID NO 2
<211> LENGTH: 225
<212> TYPE: PRT
<213> ORGANISM: Artificial
<220> FEATURE:
<223> OTHER INFORMATION: HCV NS5A domain I protein with a C-terminal
      fusion tag

<400> SEQUENCE: 2

Ser Lys Leu Leu Pro Arg Leu Pro Gly Val Pro Phe Phe Ser Cys Gln
1               5                   10                  15

Arg Gly Tyr Lys Gly Val Trp Arg Gly Asp Gly Ile Met Gln Thr Thr
            20                  25                  30

Cys Pro Cys Gly Ala Gln Ile Thr Gly His Val Lys Asn Gly Ser Met
        35                  40                  45

Arg Ile Val Gly Pro Arg Thr Cys Ser Asn Thr Trp His Gly Thr Phe
    50                  55                  60
```

```
Pro Ile Asn Ala Tyr Thr Thr Gly Pro Cys Thr Pro Ser Pro Ala Pro
 65                  70                  75                  80

Asn Tyr Ser Arg Ala Leu Trp Arg Val Ala Ala Glu Glu Tyr Val Glu
                 85                  90                  95

Val Thr Arg Val Gly Asp Phe His Tyr Val Thr Gly Met Thr Thr Asp
            100                 105                 110

Asn Val Lys Cys Pro Cys Gln Val Pro Ala Pro Glu Phe Phe Thr Glu
        115                 120                 125

Val Asp Gly Val Arg Leu His Arg Tyr Ala Pro Ala Cys Lys Pro Leu
    130                 135                 140

Leu Arg Glu Glu Val Thr Phe Leu Val Gly Leu Asn Gln Tyr Leu Val
145                 150                 155                 160

Gly Ser Gln Leu Pro Cys Glu Pro Glu Pro Asp Val Ala Val Leu Thr
                165                 170                 175

Ser Met Leu Thr Asp Pro Ser His Ile Thr Ala Glu Thr Ala Lys Arg
            180                 185                 190

Gly Thr Asp Asp Asp Lys Ala Met Ala Ile Ser Asp Pro Asn Ser
        195                 200                 205

Ser Ser Val Asp Lys Leu Ala Ala Ala Leu Glu His His His His
    210                 215                 220

His
225

<210> SEQ ID NO 3
<211> LENGTH: 6115
<212> TYPE: DNA
<213> ORGANISM: Artificial
<220> FEATURE:
<223> OTHER INFORMATION: Plasmid for HCV NS5A domain I fusion protein
      expression

<400> SEQUENCE: 3
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta aatcgggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta agggatttt gccgatttcg gcctattggt taaaaaatg agctgattta    420 acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg aattaattct tagaaaaact catcgagcat caaatgaaac tgcaattat    600 tcatatcagg attatcaata ccatattttt gaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa ataaggttat caagtgaga    780 aatcaccatg agtgacgact gaatccggtg agaatggcaa agtttatgc atttcttttc    840 agacttgttc aacaggccag ccattacgct cgtcatcaaa atcactcgca tcaaccaaac    900
cgttattcat tcgtgattgc gcctgagcga cgaaatac gcgatcgctg ttaaaggac      960 aattacaaac aggaatcgaa tgcaaccggc gcaggaacac tgccagcgca tcaacaatat  1020
```

-continued

```
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920 aaggcggaca ggtatccggt aagcggcagg gtcggaacag gagagcgcac gagggagctt    1980 ccaggggga acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg cctttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280 tatttttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aaggggatt tctgttcatg gggtaatga taccgatgaa    2760 acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactttta   3000 cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
```

```
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatgtcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgcggtga tgccggccac gatgcgtccg gcgtagagga tcgagatcga tctcgatccc    4980
gcgaaattaa tacgactcac tatagggaa ttgtgagcgg ataacaattc cccaaataat    5040
tttgtttaac tttaagaagg agatatacat atgcagatct tcgtgaagac tttgaccggt    5100
aaaaccataa cattggaagt tgaatcttcc gataccatcg acaacgttaa gtcgaaaatt    5160
caagacaagg aaggtatccc tccagatcaa caaagattga tctttgccgg taagcagcta    5220
gaagacggta gaacgctgtc tgattacaac attcagaagg agtccacctt acatctggtg    5280
ctaaggctcc gcggggggtc caaactcctg ccgcgattgc cggagtccc cttcttctca    5340
tgtcaacgtg ggtacaaggg agtctggcgg ggcgacggca tcatgcaaac cacctgccca    5400
tgtggagcac agatcaccgg acatgtgaaa aacggttcca tgaggatcgt ggggcctagg    5460
acctgtagta acacgtggca tggaacattc cccattaacg cgtacaccac gggcccctgc    5520
acgccctccc cggcgccaaa ttattctagg gcgctgtggc gggtggctgc tgaggagtac    5580
gtggaggtta cgcgggtggg ggatttccac tacgtgacgg gcatgaccac tgacaacgta    5640
aagtgcccgt gtcaggttcc ggcccccgaa ttcttcacag aagtggatgg ggtgcggttg    5700
cacaggtacg ctccagcgtg caaacccctc ctacgggagg aggtcacatt cctggtcggg    5760
```

```
ctcaatcaat acctggttgg gtcacagctc ccatgcgagc ccgaaccgga cgtagcagtg    5820
ctcacttcca tgctcaccga cccctcccac attacgcgg agacggctaa gcgtaggggt    5880
accgacgacg acgacaaggc catggcgata tcggatccga attcgagctc cgtcgacaag    5940
cttgcggccg cactcgagca ccaccaccac caccactgag atccggctgc taacaaagcc    6000
cgaaaggaag ctgagttggc tgctgccacc gctgagcaat aactagcata accccttggg    6060
gcctctaaac gggtcttgag gggttttttg ctgaaaggag gaactatatc cggat         6115

<210> SEQ ID NO 4
<211> LENGTH: 199
<212> TYPE: PRT
<213> ORGANISM: Artificial
<220> FEATURE:
<223> OTHER INFORMATION: Proteolytically cleaved HCV NS5A domain I
      fusion protein

<400> SEQUENCE: 4

Ser Lys Leu Leu Pro Arg Leu Pro Gly Val Pro Phe Phe Ser Cys Gln
1               5                   10                  15

Arg Gly Tyr Lys Gly Val Trp Arg Gly Asp Gly Ile Met Gln Thr Thr
            20                  25                  30

Cys Pro Cys Gly Ala Gln Ile Thr Gly His Val Lys Asn Gly Ser Met
        35                  40                  45

Arg Ile Val Gly Pro Arg Thr Cys Ser Asn Thr Trp His Gly Thr Phe
    50                  55                  60

Pro Ile Asn Ala Tyr Thr Thr Gly Pro Cys Thr Pro Ser Pro Ala Pro
65                  70                  75                  80

Asn Tyr Ser Arg Ala Leu Trp Arg Val Ala Ala Glu Glu Tyr Val Glu
                85                  90                  95

Val Thr Arg Val Gly Asp Phe His Tyr Val Thr Gly Met Thr Thr Asp
            100                 105                 110

Asn Val Lys Cys Pro Cys Gln Val Pro Ala Pro Glu Phe Phe Thr Glu
        115                 120                 125

Val Asp Gly Val Arg Leu His Arg Tyr Ala Pro Ala Cys Lys Pro Leu
    130                 135                 140

Leu Arg Glu Glu Val Thr Phe Leu Val Gly Leu Asn Gln Tyr Leu Val
145                 150                 155                 160

Gly Ser Gln Leu Pro Cys Glu Pro Glu Pro Asp Val Ala Val Leu Thr
                165                 170                 175

Ser Met Leu Thr Asp Pro Ser His Ile Thr Ala Glu Thr Ala Lys Arg
            180                 185                 190

Gly Thr Asp Asp Asp Lys
            195
```